US008337852B2

(12) United States Patent  (10) Patent No.: US 8,337,852 B2
Mackay  (45) Date of Patent: Dec. 25, 2012

(54) ANTI-C5AR ANTIBODIES WITH IMPROVED PROPERTIES

(75) Inventor: Charles Reay Mackay, Vaucluse (AU)

(73) Assignee: G2 Inflammation Pty Ltd, Darlinghurst (AU)

( * ) Notice: Subject to any disclaimer, the term of this patent is extended or adjusted under 35 U.S.C. 154(b) by 659 days.

(21) Appl. No.: 12/375,876

(22) PCT Filed: Aug. 22, 2007

(86) PCT No.: PCT/AU2007/001207

§ 371 (c)(1),
(2), (4) Date: Jan. 30, 2009

(87) PCT Pub. No.: WO2008/022390

PCT Pub. Date: Feb. 28, 2008

(65) Prior Publication Data

US 2010/0129346 A1    May 27, 2010

Related U.S. Application Data

(60) Provisional application No. 60/839,634, filed on Aug. 22, 2006.

(51) Int. Cl.
*A61K 39/395* (2006.01)
*C07K 16/28* (2006.01)
*G01N 33/53* (2006.01)

(52) U.S. Cl. ............... 424/144.1; 424/130.1; 424/133.1; 424/141.1; 424/143.1; 424/152.1; 530/387.1; 530/387.3; 530/388.1; 530/388.2; 435/7.1

(58) Field of Classification Search ........................ None
See application file for complete search history.

(56) References Cited

U.S. PATENT DOCUMENTS

| | | | |
|---|---|---|---|
| 3,850,752 A | 11/1974 | Schuurs et al. | |
| 3,901,654 A | 8/1975 | Gross | |
| 4,098,876 A | 7/1978 | Piasio et al. | |
| 4,676,980 A | 6/1987 | Segal et al. | |
| 4,704,362 A | 11/1987 | Itakura et al. | |
| 5,194,594 A | 3/1993 | Khawli et al. | |
| 5,284,746 A | 2/1994 | Sledziewski et al. | |
| 5,304,489 A | 4/1994 | Rosen | |
| 5,354,678 A | 10/1994 | Lebowski et al. | |
| 5,480,974 A | 1/1996 | Morgan et al. | |
| 5,741,957 A | 4/1998 | Deboer et al. | |
| 5,849,992 A | 12/1998 | Meade et al. | |
| 5,861,272 A | 1/1999 | Li et al. | |
| 8,007,798 B2 * | 8/2011 | Ashkenazi et al. | 424/145.1 |
| 8,071,096 B2 | 12/2011 | Mackay | |
| 8,071,839 B2 | 12/2011 | Mackay | |
| 8,221,757 B2 | 7/2012 | Mackay | |
| 2003/0113798 A1 | 6/2003 | Burmer et al. | |
| 2005/0084906 A1 | 4/2005 | Goetsch et al. | |
| 2011/0190477 A1 | 8/2011 | Whitfeld et al. | |

FOREIGN PATENT DOCUMENTS

| | | |
|---|---|---|
| EP | 0377489 | 7/1990 |
| EP | 0586505 | 3/1994 |
| JP | 8109200 | 4/1996 |
| WO | WO 9100360 | 1/1991 |
| WO | WO 9220373 | 11/1992 |
| WO | WO 9407921 | 4/1994 |
| WO | WO 9411026 | 5/1994 |
| WO | WO 9420142 | 9/1994 |
| WO | WO 9500164 | 1/1995 |
| WO | WO 9639511 | 12/1996 |
| WO | WO 9824893 | 6/1998 |
| WO | WO 9833908 | 8/1998 |
| WO | WO 9844001 | 10/1998 |
| WO | WO 0238767 | 5/2002 |
| WO | WO 02059263 | 8/2002 |
| WO | WO 02061087 | 8/2002 |
| WO | WO 03027252 | 4/2003 |
| WO | WO-03062278 | 7/2003 |
| WO | WO 2004040000 | 5/2004 |
| WO | WO 2005060739 | 7/2005 |
| WO | WO 2008022390 | 2/2008 |
| WO | WO 2008022391 | 2/2008 |

OTHER PUBLICATIONS

Rudikoff et al., (Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Prince, Biomarkers 10 Supplement 1: S44-S49, 2005.*
Biomarkers Definitions Working Groups., Clin. Pharmacol. Ther. 69: 89-95, 2001.*
Kuby in Immunology, Second Edition, W.H. Freeman and Company, New York, 1991; see Chapter 8, Organization and Expression of Immunoglobulin Genes on pp. 175-208.*
Nisonoff, Heterogeneity of Antibodies iin Introduction to Molecular Immunology, Second Edition, Sinauer Associates, Inc. Dunderland, MA, 1985; see Chapter 2: General Structural Properties of Antibodies on pp. 7-28.*
Kuby in Immunology, Second Edition, W.H. Freeman and Company, New York, 1991; see Chapter 4, Antigens on pp. 85-108.*
Ohno, et al., "Antigen-binding specificities of antibodies are primarily determined by seven residues of VH," Proc. Natl. Acad. Sci. USA (1985) 82:2945-2949.
Dai, et al., "Gene Therapy via Primary Myoblasts: Long-term Expression of Factor IX Protein Following Transplantation in vivo", Proc. Natl. Acad. Sci., 89:10892-10895 (1992).
Gerard, et al., "C5a Anaphylatoxin and Its Seven Transmembrane Segment Receptor", Annu. Rev. Immunol., 12:775-808 (1994).
International Search Report and Written Opinion issued for PCT/AU2007/001207, dated Nov. 8, 2007 (14 pages).
Kaneko, et al., "Antagonistic Peptides Against Human Anaphylatoxin C5a", Immunology, 86:149-154 (1995).
Konteatis, et al., "Development of C5a Receptor Antagonists" Differential Loss of Functional Responses, Journal of Immunology, 153:4200-4205 (1994).

(Continued)

*Primary Examiner* — Phillip Gambel

(74) *Attorney, Agent, or Firm* — Carol L. Francis; Bozicevic, Field & Francis LLP

(57) ABSTRACT

The present invention relates to improved antibodies which bind to C5aR and which are useful in diagnosis and therapeutic methods.

18 Claims, 16 Drawing Sheets

OTHER PUBLICATIONS

Lebkowski, et al., "Adeno-Associated Virus: a Vector System for Efficient Introduction and Integration of DNA into a Variety of Mammalian Cell Types", Molecular and Cellular Biology, 8(10):3988-3996 (1988).

Lee, et al. "Human C5aR Knock-In Mice Facilitate the Production and Assessment of Anti-Inflammatory Monoclonal Antibodies." Nature Biotechnology. 2006. vol. 24, No. 10. pp. 1279-1284.

Morgan, et al., "Antti-C5a Receptor Andibodies", Journal of Immunology, 151:377-388 (1993).

Murdoch, et al., "Chemokine Receptors and Their Role in Inflammation and Infectious Diseases", Blood, 95(10):3032-3043 (2000).

Pellas, et al., "Novel C5a Receptor Antagonists Regulate Neutrophil Functions in Vitro and In Vivo", Journal of Immunology, 150:5616-5621 (1998).

Ulmer, et al., "Heterologous Protection Against Inluenza by Injection of DNA Encoding a Viral Protein", Science, 259:1745-1749 (1993).

Watanabe, et al., "Analysis of C5a Receptor by Monoclonal Antibody", Journal of Immunological Methods, 185:19-29 (1995).

Williams, et al. "Introduction of Foreign Genes into Tissues of Living Mice by DNA-Coated Microprojectiles", Proc. Natl. Acad. Sci., 88:2726-2730 (1991).

Wu, et al., "Receptor-Mediated in Vitro Gene Transformation by a Soluble DNA Carrier System", Journal of Biological Chemistry, 262(10):4429-4432 (1997).

International Search Report and Written Opinion of the International Searching Authority, PCT/AU 2007/001207, Nov. 20, 2007 (12 pages).

Examiner's Report issued by Australian Patent Office dated Dec. 22, 2011, AU Patent Application No. 2007288188 (3 pages).

Translation of Official Action issued by Russian Patent Office dated Jan. 17, 2011, Application No. 2009110154/13(013781) (3 pages).

U.S. Appl. No. 13/525,092, filed Jun. 15, 2012, Mackay.

U.S. Appl. No. 13/590,016, filed Aug. 20, 2012, Whitfeld, et al.

Barry, et al. (1994) "Sequencing and Modeling of Anti-DNA Immunoglobulin Fv Domains. Comparison with Crystal Structures" J. Biol. Chem. 269(5):3623-3632.

Berman, et al. (1988) "Lymphocyte Motility and Lymphocyte Chemoattractant Factors" Immunol. Invest. 17(8-9):625-677.

Cain, et al. (2001) "Mapping the Ligand-Binding Site on the C5a Receptor: Arginine74 of C5a Contacts Aspartate282 of the C5a Receptor" Biochemistry 40(46):14047-14052.

Cain, et al. (2001) "Modulation of Ligand Selectivity by Mutation of the First Extracellular Loop of the Human C5a Receptor" Biochem. Pharmacol. 61(12):1571-1579.

Caldas, et al. (2000) "Design and Synthesis of Germline-Based Hemi-Humanized Single-Chain Fv against the CD18 Surface Antigen" Protein Eng. 13(5):353-360.

Caldas, et al. (2003) "Humanization of the Anti-CD18 Antibody 6.7: An Unexpected Effect of a Framework Residue in Binding to Antigen" Mol. Immunol. 39(15):941-952.

Caron, et al. (1992) "Engineered Humanized Dimeric Forms of IgG Are More Effective Antibodies" J. Exp. Med. 176(4):1191-1195.

Casset, et al. (2003) "A Peptide Mimetic of an Anti-CD4 Monoclonal Antibody by Rational Design" Biochem. Biophys. Res. Commun. 307(1):198-205.

Champtiaux & Changeux (2002) "Knock-out and knock-in mice to investigate the role of nicotinic receptors in the central nervous system" Curr Drug Targets CNS Neurol Disord 1(4):319-330.

Charlton et al. (1999) "The Expression of C5A Receptor (C5AR) (CD88) Is Associated with the Progression of Inflammation in Human Disease" J. Pathol. 187(Suppl.):36A.

Chothia & Lesk (1987) "Canonical Structures for the Hypervariable Regions of Immunoglobulins" J. Mol. Biol. 196(4):901-917.

Chothia, et al. (1989) "Conformations of Immunoglobulin Hypervariable Regions" Nature 342(6252):877-883.

Co, et al. (1992) "Chimeric and Humanized Antibodies with Specificity for the CD33 Antigen" J. Immunol. 148(4):1149-1154.

Crass, et al. (1999) "Chimeric Receptors of the Human C3a Receptor and C5a Receptor (CD88)" J. Biol. Chem. 274(13):8367-8370.

Crass, et al. (1999) "Receptor Activation by Human C5a des Arg74 but Not Intact C5a Is Dependent on an Interaction between Glu199 of the Receptor and Lys68 of the Ligand" Biochemistry 38(30):9712-9717.

Curiel, et al. (1992) "High-Efficiency Gene Transfer Mediated by Adenovirus Coupled to DNA-Polylysine Complexes" Hum. Gene Ther. 3(2):147-154.

Dahinden, et al. (1994) "Monocyte Chemotactic Protein 3 Is a Most Effective Basophil- and Eosinophil-Activating Chemokine" J. Exp. Med. 179(2):751-756.

Demartino, et al. (1995) "Arginine 206 of the C5a Receptor Is Critical for Ligand Recognition and Receptor Activation by C-Terminal Hexapeptide Analogs" J. Biol. Chem. 270(27):15966-15969.

Drago (2003) "Neuronal nicotinic receptors: insights gained from gene knockout and knockin mutant mice" Cellular Mol Life Sci 60(7):1267-1280.

Dymecki, Susan M., Flp recombinase promotes site-specific DNA recombination in embryonic stem cells and transgenic mice., Proc Natl Acad Sci U S A. Jun. 11, 1996;93(12):6191-6196.

Eigenbrot, et al. (1993) "X-ray Structures of the Antigen-Binding Domains from Three Variants of Humanized Anti-p185HER2 Antibody 4D5 and Comparison with molecular Modeling" J. Mol. Biol. 229(4):969-995.

Elsner, et al. (1994) "C3a Activates the Respiratory Burst in Human Polymorphonuclear Neutrophilic Leukocytes via Pertussis Toxin-Sensitive G-Proteins" Blood 83(11):33224-3331.

Extended European Search Report for European Application No. 10009060.4, dated Jul. 29, 2011.

Farkas, et al. (1999) "C5a Receptor Expression by TGW Neuroblastoma Cells" Neuroreport 10(14):3021-3025.

Fayyazi et al. (2000) "The C5a Receptor Is Expressed in Normal Renal Proximal Tubular but Not in Normal Pulmonary or Hepatic Epithelial Cells" Immunology 99(1):38-45.

Fitzgerald (1987) "Construction of Immunotoxins Using Pseudomonas Exotoxin A" Methods Enzymol. 151:139-145.

Gerard & Gerard (1991) "The Chemotactic Receptor for Human C5a Anaphylatoxin" Nature 349(6310):614-617.

Gerber, et al. (2001) "An Activation Switch in the Ligand Binding Pocket of the C5a Receptor" J. Biol. Chem. 276(5):3394-3400.

Girardi (2003) "Complement C5a receptors and neutrophils mediate fetal injury in the antiphospholipid syndrome" J. Clin. Invest. 112(11):1644-1654.

Gu et al. (2003) "Neuropilin-1 conveys semaphorin and VEGF signaling during neural and cardiovascular development" Dev Cell 5(1):45-57.

Hansen & Balthasar (2002) "Intravenous Immunoglobulin Mediates an Increase in Anti-Platelet Antibody Clearance via the FcRn Receptor" Thromb. Haemost. 88(6):898-899.

Heller et al. Selection of a C5a receptor antagonist from phage libraries attenuating the inflammatory response in immune complex disease and ischemia/reperfusion injury. The Journal of Immunology (1999) 163: 985-994.

Hendrickson, et al. (1995) "High Sensitivity Multianalyte Immunoassay Using Covalent DNA-Labeled Antibodies and Polymerase Chain Reaction" Nucleic Acids Res. 23(3):522-529.

Homanics (2002) "Knockout and Knockin Mice" Methods in Alcohol Related Neuroscience Research, Editor, Liu, Yuan, Chapter 2, pp. 31-61.

Höpken et al. (1996) "The C5a chemoattractant receptor mediates mucosal defence to infection" Nature 383(6595):86-89.

Hugli et al., The active site of human C4a anaphylatoxin. Mol. Immunol. 1983;20:637-45.

Jagels, et al. (1996) "Proteolytic Inactivation of the Leukocyte C5a Receptor by Proteinases Derived from Porphyromonas Gingivalis" Infect. Immun. 64(6):1984-1991.

Ji, et al. (2002) "Arthritis Critically Dependent on Innate Immune System Players" Immunity 16(2):157-168.

Jones, et al. (1986) "Replacing the Complementarity-Determining Regions in a Human Antibody with Those from a Mouse" Nature 321(6069):522-525.

Jose, et al. (1994) "Eotaxin: A Potent Eosinophil Chemoattractant Cytokine Detected in a Guinea Pig Model of Allergic Airways Inflammation" J. Exp. Med. 179(3):881-887.

Kavanaugh, et al. (1991) "Role of CD11/CD18 in Adhesion and Transendothelial Migration of T Cells. Analysis Utilizing CD18-Deficient T Cell Clones" *J. Immunol.* 146(12):4149-4156.

Kedmi et al. (2003) "Loss of Nicotine-Induced Seizures in Double-Knockout Mice with α5 and β4 Neuronal Nicotinic Acetylcholine Receptor Subunits Deficiency" Society for Neuroscience, Neuroscience 2003 Abstract, Presentation No. 533.12, Nov. 10, 2003.

Kouskoff, et al. (1996) "Organ-Specific Disease Provoked by Systemic Autoimmunity" *Cell* 87(5):811-822.

Kozlov, et al. (2004) "Efficient Strategies for the Conjugation of Oligonucleotides to Antibodies Enabling Highly Sensitive Protein Detection" *Biopolymers* 73(5):621-630.

Kyburz & Corr (2003) "The KRN Mouse Model of Inflammatory Arthritis" *Springer Semin. Immunopathol.* 25(1):79-90.

Labarca et al., "Point mutant mice with hypersensitive .alpha.4 nicotinic receptors show dopaminergic deficits and increased anxiety," PNAS, 2001, 98(5), 2786-2791.

Layton et al., "Cross-species Receptor Binding Characteristics of Human and Mouse Leukemia Inhibitory Factor Suggest a Complex Binding Interaction," J Biol. Chem., 1994, 269(25), 17048-17055.

Lee, et al. (2002) "Mast Cells: A Cellular Link between Autoantibodies and Inflammatory Arthritis" *Science* 297(5587):1689-1692.

Lester (2003) "Hypersensitive knockin mouse strains identify receptors and pathways for nicotine action" *Curr Opin Drug Discov Devel* 6(5):633-639.

Lienenklaus et al. "Cutting Edge: Human anaphylatoxin C4a is a potent agonist of the guinea pig but not the human C3a receptor" J. Immunol. 1998;161:2089-93.

Liu et al., "The α chain of the IL-2 receptor determines the species specificity of high-affinity IL-2 binding," Cytokine, 1996, 8(8), 613-621.

Lowenstein, et al. (2006) "Different Mechanisms of Campath-1H-Mediated Depletion for CD4 and CD8 T Cells in Peripheral Blood" *Transplant International* 19(11):927-936.

MacCallum, et al. (1996) "Antibody-Antigen Interactions: Contact Analysis and Binding Site Topography" *J. Mol. Biol.* 262(5):732-745.

Martin, et al. (1989) "Modeling Antibody Hypervariable Loops: A Combined Algorithm" *Proc. Natl. Acad. Sci. USA* 86(23):9268-9272.

Mayo & Curnutte (1990) "Kinetic Microplate Assay for Superoxide Production by Neutrophils and Other Phagocytic Cells" *Methods Enzymol.* 186:567-575.

Monk, et al. (1995) "Mutation of Glutamate 199 of the Human C5a Receptor Defines a Binding Site for Ligand Distinct from the Receptor N Terminus" *J. Biol. Chem.* 270(28):16625-16629.

Monk, et al. (2007) "Function, Structure and Therapeutic Potential of Complement C5a Receptors" *Br. J. Pharmacol.* 152(4):429-448.

Mosmann et al., "Species-specificity of T cell stimulating activities of IL 2 and BSF-1 (IL 4): comparison of normal and recombinant, mouse and human IL 2 and BSF-1 (IL 4)," J. Immunol., 1987, 138, 1813-1816.

Mukherjee et al., The role of complement anaphylatoxin C5a in neurodegradation: Implications in Alzheimer's Disease. J Neuroimmunol 2000;105(2)124-30.

Muller, Ten years of gene targeting: targeted mouse mutants, from vector design to phenotype analysis. Mech. Dev. 1999;82:3-21.

Needleman & Wunsch (1970) "A General Method Applicable to the Search for Similarities in the Amino Acid Sequence of Two Proteins" *J. Mol. Biol.* 48(3):444-453.

Neote, et al. (1993) "Molecular Cloning, Functional Expression, and Signaling Characteristics of a C-C Chemokine Receptor" *Cell* 72(3):415-425.

Niemeyer, et al. (2003) "Combination of DNA-Directed Immobilization and Immuno-PCR: Very Sensitive Antigen Detection by Means of Self-Assembled DNA-Protein Conjugates" *Nucl. Acids Res.* 31(16):e90.

Nisihara, et al. (2001) "Humanization and Epitope Mapping of Neutralizing Anti-Human Fas Ligand Monoclonal Antibodies: Structural Insights into Fas/Fas Ligand Interaction" *J. Immunol.* 167(6):3266-3275.

Oppermann, et al. (1993) "Probing the Human Receptor for C5a Anaphylatoxin with Site-Directed Antibodies. Identification of a Potential Ligand Binding Site on the NH2-Terminal Domain" *J. Immunol.* 151(7):3785-3794.

Pease, et al. (1994) "Generation of Chimeric C5a/Formyl Peptide Receptors: Towards the Identification of the Human C5a Receptor Binding Site" *Eur. J. Immunol.* 24(1):211-215.

Preithner, et al. (2006) "High Concentrations of Therapeutic IgG1 Antibodies Are Needed to Compensate for Inhibition of Antibody-Dependent Cellular Cytotoxicity by Excess Endogenous Immunoglobulin G" *Mol. Immunol.* 43(8):1183-1189.

Proctor, et al. (2006) "Recent Developments in C5/C5a Inhibitors" *Expert Opinion on Therapeutic Patents* 16(4):445-458.

Prosser, et al. (2002) "Targeted replacement of rodent CCR2 with the human orthologue CCR2B: A mouse model for in vivo analysis of human target-selective small molecule MCP-1 receptor antagonists" *Drug Development Research* 55(4):197-209.

Pulito, et al. (1996) "Humanization and Molecular Modeling of the Anti-CD4 Monoclonal Antibody, OKT4A" *J. Immunol.* 156(8):2840-2850.

Queen, et al. (1986) "Cell-Type Specific Regulation of a Kappa Immunoglobulin Gene by Promoter and Enhancer Elements" *Immunol. Rev.* 89:49-68.

Raffetseder, et al. (1996) "Site-Directed Mutagenesis of Conserved Charged Residues in the Helical Region of the Human C5a Receptor. Arg2O6 Determines High-Affinity Binding Sites of C5a Receptor" Eur. J. Biochem. 235 (1-2):82-90.

Roebroek (2003) "Knockin approaches" *Methods Mol Biol* 209:187-200.

Rothermel, et al. (2000) "Analysis of the Tissue Distribution of the Rat C5a Receptor and Inhibition of C5a-Mediated Effects through the Use of Two MoAbs" Scand. J. Immunol. 52(4):401-410.

Rozmahel (1997) "Incomplete rescue of cystic fibrosis transmembrane conductance regulator deficient mice by the human CFTR cDNA" *Hum Mol Genet* 6(7):1153-1162.

Sato (1999) "Gene trap, gene knockout, gene knock-in, and transgenics in vascular development" *Thromb Haemost* 82(2):865-869.

Sayah, et al. (1999) "Expression of Cytokines by Human Astrocytomas Following Stimulation by C3a Anaphylatoxins: Specific Increase in Interleukin-6 mRNA Expression" *J. Neurochem.* 72(6):2426-2436.

Schlaf, et al. (1999) "Differential Expression of the C5a Receptor on the Main Cell Types of Rat Liver as Demonstrated with a Novel Monoclonal Antibody and by C5a Anaphylatoxin-Induced Ca2+ Release" *Lab. Invest.* 79(10):1287-1297.

Shopes (1992) "A Genetically Engineered Human IgG Mutant with Enhanced Cytolytic Activity" *J. Immunol.* 148(9):2918-2922.

Smith et al., "Species Specificity of Human and Murine Tumor Necrosos factor," J. Biol. Chem., 1986, 261(32), 14871-14874.

Solomon, et al. (2005) "A Crucial Role for Macrophages in the Pathology of K/B x N Serum-Induced Arthritis" *Eur. J. Immunol.* 35(10):3064-3073.

Stevenson, et al. (1989) "A Chimeric Antibody with Dual Fc Regions (bisFabFc) Prepared by Manipulations at the IgG Hinge" *Anticancer Drug Design* 3(4):219-230.

Takeuchi,et al., Flp recombinase transgenic mice of C57BL/6 strain for conditional gene targeting., Biochem Biophys Res Commun. May 10, 2002;293(3):953-957.

Van Damme, et al. (1992) "Structural and Functional Identification of Two Human, Tumor-Derived Monocyte Chemotactic Proteins (MCP-2 and MCP-3) Belonging to the Chemokine Family" *J. Exp. Med.* 176(1):59-65.

Van Meerten, et al. (2006) "Complement-Induced Cell Death by Rituximab Depends on CD20 Expression Level and Acts Complementary to Antibody-Dependent Cellular Cytotoxicity" *Clin. Cancer Res.* 12(13):4027-4035.

Van Riper, et al. (1993) "Characterization and Species Distribution of High Affinity GTP-Coupled Receptors for Human Rantes and Monocyte Chemoattractant Protein 1" *J. Exp. Med.* 177(3):851-856.

Verhoeyen, et al. (1988) "Reshaping Human Antibodies: Grafting an Antilysozyme Activity" *Science* 239(4847):1534-1536.

Vitetta (1993) "Immunotoxins: Magic Bullets or Misguided Missiles?" *Immunol. Today* 14(6):252-259.

Vitetta, et al. (1987) "Redesigning Nature's Poisons to Create Anti-Tumor Reagents" *Science* 238(4830):1098-1104.

Wang et al. (2002) "Gain-Of Function Mutation of Human Erythropoietin Receptor in Mice Decreases Neointimal Formation" *Blood* 11(11): Abstract No. 2681.

Whitfeld, et al. (2007) "Novel mAbs to C5aR $2^{nd}$ Loop Reverse Disease in Models of Inflammatory Arthritis" *Inflamm. Res.* 56(Suppl. 3):S401.

Wipke & Allen (2001) "Essential Role of Neutrophils in the Initiation and Progression of a Murine Model of Rheumatoid Arthritis" *J. Immunol.* 167(3):1601-1608.

Wolff, et al. (1993) "Monoclonal Antibody Homodimers: Enhanced Antitumor Activity in Nude Mice" *Cancer Res.* 53(11):2560-2565.

Woodruff et al. (2001) "Species dependence for binding of small molecule agonist and antagonists to the C5a receptor on polymorphonuclear leukocytes" *Inflammation* 25(3):171-177.

Woodruff et al. (2002) "Antiarthritic activity of an orally active C5a receptor antagonist against antigen-induced monarticular arthritis in the rat" *Arthritis Rheum* 46(9):2476-2485.

Wu (2003) "Simultaneous Humanization and Affinity Optimization of Monoclonal Antibodies" *Methods Mol. Biol.* 207:197-212.

Wu, et al. (1999) "Humanization of a Murine Monoclonal Antibody by Simultaneous Optimization of Framework and CDR Residues" *J. Mol. Biol.* 294(1):151-162.

Zachariae, et al. (1990) "Properties of Monocyte Chemotactic and Activating Factor (MCAF) purified from a Human Fibrosarcoma Cell Line" *J. Exp. Med.* 171(6):2177-2182.

Gerard et al. (1993) "Human chemotaxis receptor genes cluster at 19q13.3-13.4. Characterization of the human C5a receptor gene" Biochemistry 32(5):1243-1250.

Köhl (2001) "Anaphylatoxins and infectious and non-infectious inflammatory diseases" Mol Immunol 38(2-3):175-187.

Wong (1999) "Development of C5a Receptor Antagonists" IDrugs 2(7):686-693.

\* cited by examiner

| Chimeric receptor | mAbs binding 2nd ECL | mAbs binding N-term | anti-mouse C5aR mAb (20/70) |
|---|---|---|---|
| HHHH | +++ | +++ | - |
| mHHH | +++ | - | - |
| mmHH | +++ | - | - |
| mmmH | - | - | +++ |
| mmmm | - | - | +++ |
| HmHH | + | - | - |
| HHmH | - | +++ | +++ |
| HHHm | + | +++ | - |
| Hmmm | - | + | +++ |
| mHmm | - | - | +++ |
| mmHm | ++ | - | - |

Figure 8

SEQUENCE LISTING

```
<160> NUMBER OF SEQ ID NOS: 63

<210> SEQ ID NO 1
<211> LENGTH: 350
<212> TYPE: PRT
<213> ORGANISM: Homo sapiens

<400> SEQUENCE: 1

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30
```

```
Leu Arg Val Pro Asp Ile Leu Ala Leu Val Ile Phe Ala Val Val Phe
         35                  40                  45

Leu Val Gly Val Leu Gly Asn Ala Leu Val Val Trp Val Thr Ala Phe
 50                  55                  60

Glu Ala Lys Arg Thr Ile Asn Ala Ile Trp Phe Leu Asn Leu Ala Val
 65                  70                  75                  80

Ala Asp Phe Leu Ser Cys Leu Ala Leu Pro Ile Leu Phe Thr Ser Ile
                 85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
            260                 265                 270

Pro Thr Phe Leu Leu Leu Asn Lys Leu Asp Ser Leu Cys Val Ser Phe
        275                 280                 285

Ala Tyr Ile Asn Cys Cys Ile Asn Pro Ile Ile Tyr Val Val Ala Gly
290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
            340                 345                 350

<210> SEQ ID NO 2
<211> LENGTH: 33
<212> TYPE: PRT
<213> ORGANISM: Homo sapiens

<400> SEQUENCE: 2

Leu Tyr Arg Val Val Arg Glu Glu Tyr Phe Pro Pro Lys Val Leu Cys
 1               5                  10                  15

Gly Val Asp Tyr Ser His Asp Lys Arg Arg Glu Arg Ala Val Ala Ile
                20                  25                  30

Val

<210> SEQ ID NO 3
<211> LENGTH: 119
<212> TYPE: PRT
```

<213> ORGANISM: Mus musculus

<400> SEQUENCE: 3

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Asn Tyr Trp Asn Trp Ile Arg Gln Phe Pro Gly Lys Lys Leu Glu Trp
        35                  40                  45

Met Gly His Ile Ser Tyr Asp Gly Asn Asn Lys Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Arg Leu Asn Ser Val Thr Ala Glu Asp Thr Ala Ala Tyr Tyr Cys
                85                  90                  95

Ala Leu Phe Tyr Phe Asp Tyr Ala Ser Phe Thr Tyr Trp Gly Gln Gly
            100                 105                 110

Thr Leu Val Thr Val Ser Ala
            115

<210> SEQ ID NO 4
<211> LENGTH: 112
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Arg Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
            100                 105                 110

<210> SEQ ID NO 5
<211> LENGTH: 119
<212> TYPE: PRT
<213> ORGANISM: Mus musculus

<400> SEQUENCE: 5

Glu Val Lys Leu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Gly Ile Arg Asn Arg Ala Asn Asn His Ala Thr Tyr Tyr Val Ala
    50                  55                  60

Ser Val Lys Gly Arg Phe Thr Val Ser Arg Asp Asp Ser Lys Ser Ser
65                  70                  75                  80

```
Val Tyr Leu Gln Met Asn Ser Leu Arg Ala Glu Asp Ala Gly Ile Tyr
            85                  90                  95

Tyr Cys Thr Arg Gly Asp Gly Tyr Phe Phe Asp Tyr Trp Gly Gln Gly
            100                 105                 110

Thr Thr Leu Thr Val Ser Ser
            115

<210> SEQ ID NO 6
<211> LENGTH: 112
<212> TYPE: PRT
<213> ORGANISM: Mus musculus

<400> SEQUENCE: 6

Asp Val Val Leu Thr Gln Thr Pro Leu Ser Leu Ser Val Ser Leu Gly
1               5                   10                  15

Asp Gln Ala Ser Ile Ser Cys Arg Ser Gly Gln Ser Leu Val His Ser
            20                  25                  30

Asn Gly Asn Thr Tyr Leu His Trp Tyr Leu Gln Lys Pro Gly Gln Ser
        35                  40                  45

Ser Lys Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Pro Thr Phe Gly Gly Gly Thr Lys Leu Glu Ile Lys
            100                 105                 110

<210> SEQ ID NO 7
<211> LENGTH: 119
<212> TYPE: PRT
<213> ORGANISM: Mus musculus

<400> SEQUENCE: 7

Asp Ile Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

His Tyr Trp Asn Trp Ile Arg Gln Leu Pro Gly Asn Lys Met Glu Trp
        35                  40                  45

Met Gly His Ile Ser Asn Asp Gly Ser Asn Arg Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Leu Phe Tyr Phe Ala Tyr Ala Ser Phe Ala Tyr Trp Gly Gln Gly
            100                 105                 110

Thr Leu Val Thr Val Ser Ala
            115

<210> SEQ ID NO 8
<211> LENGTH: 112
<212> TYPE: PRT
<213> ORGANISM: Mus musculus

<400> SEQUENCE: 8

Asp Val Val Met Thr Gln Thr Pro Leu Ser Leu Pro Val Ser Leu Gly
1               5                   10                  15
```

```
Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Thr Arg Phe Ser Gly Val Pro
    50                  55                  60

Asp Arg Phe Ser Gly Ser Gly Ser Gly Ala Asp Phe Thr Leu Gln Ile
65                  70                  75                  80

Ser Arg Val Glu Ala Glu Asp Leu Gly Val Tyr Leu Cys Ser Gln Ser
                85                  90                  95

Thr His Val Pro Pro Thr Phe Gly Ala Gly Thr Lys Leu Val Leu Thr
            100                 105                 110

<210> SEQ ID NO 9
<211> LENGTH: 37
<212> TYPE: PRT
<213> ORGANISM: Homo sapiens

<400> SEQUENCE: 9

Ser Gly Ser Gly Leu Tyr Arg Val Val Arg Glu Glu Tyr Phe Pro Pro
1               5                   10                  15

Lys Val Leu Cys Gly Val Asp Tyr Ser His Asp Lys Arg Arg Glu Arg
            20                  25                  30

Ala Val Ala Ile Val
        35

<210> SEQ ID NO 10
<211> LENGTH: 46
<212> TYPE: DNA
<213> ORGANISM: Artificial
<220> FEATURE:
<223> OTHER INFORMATION: oligonucleotide

<400> SEQUENCE: 10
cgtttaaact taagcttgcc accatggacc ccatagataa cagcag              46

<210> SEQ ID NO 11
<211> LENGTH: 41
<212> TYPE: DNA
<213> ORGANISM: Artificial
<220> FEATURE:
<223> OTHER INFORMATION: oligonucleotide

<400> SEQUENCE: 11
ggcaacctgg ggatgttgca gccttggtca tctttgcagt c                   41

<210> SEQ ID NO 12
<211> LENGTH: 44
<212> TYPE: DNA
<213> ORGANISM: Artificial
<220> FEATURE:
<223> OTHER INFORMATION: oligonucleotide

<400> SEQUENCE: 12
ccagtagtta tgatttaaaa cggtcgtgaa caagatgggc agcg                44

<210> SEQ ID NO 13
<211> LENGTH: 41
<212> TYPE: DNA
<213> ORGANISM: Artificial
<220> FEATURE:
<223> OTHER INFORMATION: oligonucleotide
```

<400> SEQUENCE: 13
atgccaccgc ctgtatagtc ctgccctccc tcatcctgct c    41

<210> SEQ ID NO 14
<211> LENGTH: 43
<212> TYPE: DNA
<213> ORGANISM: Artificial
<220> FEATURE:
<223> OTHER INFORMATION: oligonucleotide

<400> SEQUENCE: 14
ccttatatgc ctcccggtac acgaaggagg gtatggtcag cag    43

<210> SEQ ID NO 15
<211> LENGTH: 39
<212> TYPE: DNA
<213> ORGANISM: Artificial
<220> FEATURE:
<223> OTHER INFORMATION: oligonucleotide

<400> SEQUENCE: 15
agaaggctgt ggccatcctg cggctggtcc tgggcttcc    39

<210> SEQ ID NO 16
<211> LENGTH: 39
<212> TYPE: DNA
<213> ORGANISM: Artificial
<220> FEATURE:
<223> OTHER INFORMATION: oligonucleotide

<400> SEQUENCE: 16
ggcagccacg ctatcatcac ccccgtcacc tggtagggc    39

<210> SEQ ID NO 17
<211> LENGTH: 42
<212> TYPE: DNA
<213> ORGANISM: Artificial
<220> FEATURE:
<223> OTHER INFORMATION: oligonucleotide

<400> SEQUENCE: 17
aagagggtgg agaagctgaa ctccctgtgt gtctcctttg cc    42

<210> SEQ ID NO 18
<211> LENGTH: 24
<212> TYPE: DNA
<213> ORGANISM: Artificial
<220> FEATURE:
<223> OTHER INFORMATION: oligonucleotide

<400> SEQUENCE: 18
cctctagagt taggccgggg ccac    24

<210> SEQ ID NO 19
<211> LENGTH: 41
<212> TYPE: DNA
<213> ORGANISM: Artificial
<220> FEATURE:
<223> OTHER INFORMATION: oligonucleotide

<400> SEQUENCE: 19
gactgcaaag atgaccaagg ctgcaacatc cccaggttgc c    41

<210> SEQ ID NO 20
<211> LENGTH: 44
<212> TYPE: DNA

```
<213> ORGANISM: Artificial
<220> FEATURE:
<223> OTHER INFORMATION: oligonucleotide

<400> SEQUENCE: 20
cgctgcccat cttgttcacg accgttttaa atcataacta ctgg          44

<210> SEQ ID NO 21
<211> LENGTH: 41
<212> TYPE: DNA
<213> ORGANISM: Artificial
<220> FEATURE:
<223> OTHER INFORMATION: oligonucleotide

<400> SEQUENCE: 21
agcaggatga gggagggcag gactatacag gcggtggcat c             41

<210> SEQ ID NO 22
<211> LENGTH: 42
<212> TYPE: DNA
<213> ORGANISM: Artificial
<220> FEATURE:
<223> OTHER INFORMATION: oligonucleotide

<400> SEQUENCE: 22
ctgctgacca taccctcctt cgtgtaccgg gaggcatata ag            42

<210> SEQ ID NO 23
<211> LENGTH: 39
<212> TYPE: DNA
<213> ORGANISM: Artificial
<220> FEATURE:
<223> OTHER INFORMATION: oligonucleotide

<400> SEQUENCE: 23
aggaagccca ggaccagccg caggatggcc acagccttc                39

<210> SEQ ID NO 24
<211> LENGTH: 39
<212> TYPE: DNA
<213> ORGANISM: Artificial
<220> FEATURE:
<223> OTHER INFORMATION: oligonucleotide

<400> SEQUENCE: 24
gccctaccag gtgacggggg tgatgatagc gtggctgcc                39

<210> SEQ ID NO 25
<211> LENGTH: 43
<212> TYPE: DNA
<213> ORGANISM: Artificial
<220> FEATURE:
<223> OTHER INFORMATION: oligonucleotide

<400> SEQUENCE: 25
ggcaaaggag acacacaggg agttcagctt ctccaccctc ttc           43

<210> SEQ ID NO 26
<211> LENGTH: 37
<212> TYPE: PRT
<213> ORGANISM: Homo sapiens

<400> SEQUENCE: 26

Ser Gly Ser Gly Leu Tyr Arg Val Val Arg Glu Glu Tyr Phe Pro Pro
1               5                   10                  15

Lys Val Leu Cys Gly Val Asp Tyr Ser His Asp Lys Arg Arg Glu Arg
```

```
                    20                  25                  30
Ala Val Ala Ile Val
        35

<210> SEQ ID NO 27
<211> LENGTH: 6
<212> TYPE: PRT
<213> ORGANISM: Artificial
<220> FEATURE:
<223> OTHER INFORMATION: peptide comprising residues 179 to 184 of Homo
      sapiens C5aR second extracellular loop

<400> SEQUENCE: 27

Glu Glu Tyr Phe Pro Pro
1               5

<210> SEQ ID NO 28
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 28

Leu Tyr Arg Val Val Arg Glu Glu Tyr Phe Pro Pro
1               5                   10

<210> SEQ ID NO 29
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 29

Tyr Arg Val Val Arg Glu Glu Tyr Phe Pro Pro Lys
1               5                   10

<210> SEQ ID NO 30
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 30

Arg Val Val Arg Glu Glu Tyr Phe Pro Pro Lys Val
1               5                   10

<210> SEQ ID NO 31
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 31

Val Val Arg Glu Glu Tyr Phe Pro Pro Lys Val Leu
1               5                   10

<210> SEQ ID NO 32
<211> LENGTH: 12
<212> TYPE: PRT
<213> ORGANISM: Artificial
```

```
<220> FEATURE:
<223> OTHER INFORMATION: peptide derived from Homo sapiens C5aR second
      extracellular loop

<400> SEQUENCE: 32

Val Arg Glu Glu Tyr Phe Pro Pro Lys Val Leu Cys
1               5                   10

<210> SEQ ID NO 33
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 33

Arg Glu Glu Tyr Phe Pro Pro Lys Val Leu Cys Gly
1               5                   10

<210> SEQ ID NO 34
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 34

Glu Glu Tyr Phe Pro Pro Lys Val Leu Cys Gly Val
1               5                   10

<210> SEQ ID NO 35
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 35

Glu Tyr Phe Pro Pro Lys Val Leu Cys Gly Val Asp
1               5                   10

<210> SEQ ID NO 36
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 36

Tyr Phe Pro Pro Lys Val Leu Cys Gly Val Asp Tyr
1               5                   10

<210> SEQ ID NO 37
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 37

Phe Pro Pro Lys Val Leu Cys Gly Val Asp Tyr Ser
1               5                   10
```

```
<210> SEQ ID NO 38
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 38

Pro Pro Lys Val Leu Cys Gly Val Asp Tyr Ser His
1               5                   10

<210> SEQ ID NO 39
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 39

Pro Lys Val Leu Cys Gly Val Asp Tyr Ser His Asp
1               5                   10

<210> SEQ ID NO 40
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 40

Lys Val Leu Cys Gly Val Asp Tyr Ser His Asp Lys
1               5                   10

<210> SEQ ID NO 41
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 41

Val Leu Cys Gly Val Asp Tyr Ser His Asp Lys Arg
1               5                   10

<210> SEQ ID NO 42
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 42

Leu Cys Gly Val Asp Tyr Ser His Asp Lys Arg Arg
1               5                   10

<210> SEQ ID NO 43
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 43
```

```
Cys Gly Val Asp Tyr Ser His Asp Lys Arg Arg Glu
1               5                   10

<210> SEQ ID NO 44
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 44

Gly Val Asp Tyr Ser His Asp Lys Arg Arg Glu Arg
1               5                   10

<210> SEQ ID NO 45
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 45

Val Asp Tyr Ser His Asp Lys Arg Arg Glu Arg Ala
1               5                   10

<210> SEQ ID NO 46
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 46

Asp Tyr Ser His Asp Lys Arg Arg Glu Arg Ala Val
1               5                   10

<210> SEQ ID NO 47
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 47

Tyr Ser His Asp Lys Arg Arg Glu Arg Ala Val Ala
1               5                   10

<210> SEQ ID NO 48
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 48

Ser His Asp Lys Arg Arg Glu Arg Ala Val Ala Ile
1               5                   10

<210> SEQ ID NO 49
<211> LENGTH: 12
<212> TYPE: PRT
<213> ORGANISM: Artificial
<220> FEATURE:
<223> OTHER INFORMATION: peptide derived from Homo sapiens C5aR second
```

-continued

```
extracellular loop

<400> SEQUENCE: 49

His Asp Lys Arg Arg Glu Arg Ala Val Ala Ile Val
1               5                   10

<210> SEQ ID NO 50
<211> LENGTH: 12
<212> TYPE: PRT
<213> ORGANISM: Artificial
<220> FEATURE:
<223> OTHER INFORMATION: peptide derived from Homo sapiens C5aR second
      extracellular loop

<400> SEQUENCE: 50

Leu Tyr Arg Val Val Arg Glu Glu Tyr Phe Pro Pro
1               5                   10

<210> SEQ ID NO 51
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 51

Val Arg Glu Glu Tyr Phe Pro Pro Lys Val Leu Ala
1               5                   10

<210> SEQ ID NO 52
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 52

Val Arg Glu Glu Tyr Phe Pro Pro Lys Val Ala Cys
1               5                   10

<210> SEQ ID NO 53
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 53

Val Arg Glu Glu Tyr Phe Pro Pro Lys Ala Leu Cys
1               5                   10

<210> SEQ ID NO 54
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 54

Val Arg Glu Glu Tyr Phe Pro Pro Ala Val Leu Cys
1               5                   10

<210> SEQ ID NO 55
<211> LENGTH: 12
```

```
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 55

Val Arg Glu Glu Tyr Phe Pro Ala Lys Val Leu Cys
1               5                   10

<210> SEQ ID NO 56
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 56

Val Arg Glu Glu Tyr Phe Ala Pro Lys Val Leu Cys
1               5                   10

<210> SEQ ID NO 57
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 57

Val Arg Glu Glu Tyr Ala Pro Pro Lys Val Leu Cys
1               5                   10

<210> SEQ ID NO 58
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 58

Val Arg Glu Glu Ala Phe Pro Pro Lys Val Leu Cys
1               5                   10

<210> SEQ ID NO 59
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 59

Val Arg Glu Ala Tyr Phe Pro Pro Lys Val Leu Cys
1               5                   10

<210> SEQ ID NO 60
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 60

Val Arg Ala Glu Tyr Phe Pro Pro Lys Val Leu Cys
1               5                   10
```

```
<210> SEQ ID NO 61
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 61

Val Ala Glu Glu Tyr Phe Pro Pro Lys Val Leu Cys
1               5                   10

<210> SEQ ID NO 62
<211> LENGTH: 12
<212> TYPE: PRT
<213> ORGANISM: Artificial
<220> FEATURE:
<223> OTHER INFORMATION: Alanine mutant of the peptide sequence
      VREEYFPPKVLC from Homo sapiens C5aR

<400> SEQUENCE: 62

Ala Arg Glu Glu Tyr Phe Pro Pro Lys Val Leu Cys
1               5                   10

<210> SEQ ID NO 63
<211> LENGTH: 12
<212> TYPE: PRT
<213> ORGANISM: Artificial
<220> FEATURE:
<223> OTHER INFORMATION: peptide comprising scrambled of VREEYFPPKVLC
      peptide derived from Homo sapiens C5aR

<400> SEQUENCE: 63

Pro Cys Tyr Val Leu Glu Lys Pro Glu Phe Val Arg
1               5                   10
```

ANTI-C5AR ANTIBODIES WITH IMPROVED PROPERTIES

CROSS REFERENCE TO RELATED APPLICATIONS

This application is a national stage application under 35 U.S.C. §371 of International Patent Appln. PCT/AU2007/001207, designating the United States and filed on Aug. 22, 2007, which claims the benefit of priority under 35 U.S.C. §119(a) to U.S. Appln. No. 60/839,634, filed Aug. 22, 2006, each of which is incorporated herein by reference.

FIELD OF THE INVENTION

The present invention relates to improved antibodies which bind to C5aR and which are useful in diagnostic and therapeutic methods.

BACKGROUND OF THE INVENTION

Proteolysis of each of the complement proteins C3-C5 gives rise to aminoterminal cationic fragments with signalling molecules called anaphylatoxins (6-9). The most potent of these, C5a, elicits the broadest responses. Considering the components of the inflammatory response as margination and infiltration of leukocytes, release of granule-bound proteolytic enzymes, production of activated oxygen and nitrogen-derived radicals, changes in blood flow and capillary leakage, along with the ability to contract smooth muscle, the C5a molecule is the "complete" pro-inflammatory mediator. At sub-nanomolar to nanomolar levels, the C5a molecule elicits chemotaxis of all myeloid lineages (neutrophils, eosinophils and basophils, macrophages and monocytes), and causes vascular permeability which is markedly potentiated by prostaglandins and circulating leukocytes. Higher nanomolar concentrations elicit degranulation and activation of NADPH oxidase. This breadth of bioactivity contrasts with other inflammatory mediators. C5a has been implicated in the pathogenesis of rheumatoid arthritis, psoriasis, sepsis, reperfusion injury, and adult respiratory distress syndrome (Gerard, et al. *Ann. Rev. Immunol.* 12:775-808 (1994); Murdoch, et al. *Blood* 95(10):3032-43 (2000)).

The activities of C5a are mediated by the binding of the C5a to its receptor (C5aR). C5aR belongs to the family of seven transmembrane G-protein-coupled receptors. C5aR is a high affinity receptor for C5a, with a $K_d$ of about 1nM, and is located on a number of different cell types including leukocytes. The number of receptors per cell is extremely high, up to 200,000 sites per leukocyte. Biological activation of the receptor occurs over the range that saturates binding.

The C5aR structure conforms to the seven transmembrane receptor family, with the extracellular N-terminus being followed by seven transmembrane helices connected by interhelical domains alternating as intracellular and extracellular loops, and ending with an intracellular C-terminal domain. C5aR contains an extended N-terminal extracellular domain. This large N-terminal domain is typical of G-protein coupled receptors which bind peptides including the IL-8 and fMet-Leu-Phe (FMLP) receptor families.

Inhibition of the C5a responses with C5aR antagonists should reduce the acute inflammatory response mediated via C5a without affecting other complement components. To this end, C5aR peptide antagonists and anti-C5a receptor antibodies have been previously described (Watanabe, et al. *J. Immunol. Meth.* 185(1):19-29 (1995); Pellas, et al. *J. Immunol.* 160(11):5616-21 (1998); Konteatis, et al. *J. Immunol.* 153(9): 4200-5 (1994); Kaneko, et al. *Immunol.* 86(1):149-54 (1995); Morgan, et al. *J. Immunol.* 151(1):377.88 (1993)). For example, WO 95/00164 (Scripps Research Inst.) describes antibodies directed against an N-terminal peptide (residues 9-29) of the C5a receptor.

WO 03/062278 (G2 Therapies) describes antibodies directed to extracellular loops of C5aR other than the N-terminal domain which are effective in inhibiting C5a binding to C5aR. Specific monoclonal antibodies disclosed in this application are MAb 7F3, MAb 12D4 and MAb 6C12. Of these monoclonal antibodies, MAb 7F3 has the highest binding affinity for C5aR.

SUMMARY OF THE INVENTION

The present inventors have now developed novel monoclonal antibodies which have substantially improved binding affinities for C5aR when compared to MAb 7F3 and are highly effective in reversing inflammation in a mouse arthritis model.

Accordingly, the present invention provides an antibody comprising at least one CDR loop sequence which shares at least 80% identity with a variable heavy chain CDR1, CDR2 or CDR3 loop sequence as shown in SEQ ID NO:3 [3C5 Vh], wherein the antibody reduces or inhibits the binding of C5a to C5aR.

In a preferred embodiment, the antibody comprises at least two CDR loop sequences which share at least 80% identity with the variable heavy chain CDR1, CDR2 or CDR3 loop sequences shown in SEQ ID NO:3 [3C5 Vh].

In a further preferred embodiment, the antibody further comprises at least one CDR loop sequence which shares at least 80% identity with a variable light chain CDR1, CDR2 or CDR3 loop sequence as shown in SEQ ID NO:4 [3C5 Vl].

In a further preferred embodiment, the antibody comprises at least two CDR loop sequences which share at least 80% identity with variable light chain CDR1, CDR2 or CDR3 loop sequence as shown in SEQ ID NO:4 [3C5 Vl].

In a further preferred embodiment, the antibody comprises a sequence which shares at least 80% identity with heavy and/or light chain sequences as shown in SEQ ID NO:3 and SEQ ID NO:4 respectively, wherein the antibody reduces or inhibits the binding of C5a to C5aR.

In a preferred embodiment the antibody binds to human C5aR or a fragment thereof with (i) an IC50 value that is at least 1.5 fold lower than that of MAb7F3 when determined under identical conditions; or (ii) an association constant (Kon) that is at least 1.5 fold higher than that of MAb7F3 when determined under identical conditions; or (iii) a $K_d$ affinity constant that is at least 1.3 fold lower than that of MAb7F3 when determined under identical conditions.

Preferably, the antibody binds to human C5aR or a fragment thereof with a $K_d$ affinity constant that is at least 1.4 fold lower than that of MAb7F3 when determined under identical conditions.

In a further preferred embodiment the antibody binds to human C5aR or a fragment thereof with (i) an $IC_{50}$ value that is less than 500 pM, preferably less than 300 pM, and more preferably less than 200 pM; or (ii) an association constant (Kon) that is at least $6.8 \times 10^5$ $M^{-1}s^{-1}$; or (iii) a $K_d$ affinity constant that is less than 1.4 nM. Preferably, the antibody binds to human C5aR or a fragment thereof with (ii) an association constant (Kon) that is at least $10^6$ $M^{-1}s^{-1}$; or (iii) a $K_d$ affinity constant that is less than 0.5 nM. Preferable, the fragment of C5aR is a peptide comprising the sequence LYRVVREEYFPPKVLCGVDYSHDKRRERAVAIV (SEQ ID NO: 2).

The present invention also provides an antibody comprising at least one CDR loop sequence which shares at least 80% identity with a variable heavy chain CDR1, CDR2 or CDR3 loop sequence as shown in SEQ ID NO:5 [7H3 Vh], wherein the antibody reduces or inhibits the binding of C5a to C5aR.

In a further preferred embodiment, the antibody comprises at least two CDR loop sequences which share at least 80% identity with the variable heavy chain CDR1, CDR2 or CDR3 loop sequences shown in SEQ ID NO:5 [7H3 Vh].

In a further preferred embodiment, the antibody further comprises at least one CDR loop sequence which shares at least 80% identity with a variable light chain CDR1, CDR2 or CDR3 loop sequence as shown in SEQ ID NO:6 [7H3 Vl].

In a further preferred embodiment, the antibody comprises at least two CDR loop sequences which share at least 80% identity with variable light chain CDR1, CDR2 or CDR3 loop sequence as shown in SEQ ID NO:6 [7H3 Vl].

In a further preferred embodiment, the antibody comprises a sequence which shares at least 80% identity with heavy and/or light chain sequences as shown in SEQ ID NO:5 and SEQ ID NO:6 respectively, wherein the antibody reduces or inhibits the binding of C5a to C5aR.

The present invention further provides an antibody comprising at least one CDR loop sequence which shares at least 80% identity with a variable heavy chain CDR1, CDR2 or CDR3 loop sequence as shown in SEQ ID NO:7 [8G7 Vh], wherein the antibody reduces or inhibits the binding of C5a to C5aR.

In a further preferred embodiment, the antibody comprises at least two CDR loop sequences which share at least 80% identity with the variable heavy chain CDR1, CDR2 or CDR3 loop sequences shown in SEQ ID NO:7 [8G7 Vh].

In a further preferred embodiment, the antibody further comprises at least one CDR loop sequence which shares at least 80% identity with a variable light chain CDR1, CDR2 or CDR3 loop sequence as shown in SEQ ID NO:8 [8G7 Vl].

In a further preferred embodiment, the antibody comprises at least two CDR loop sequences which share at least 80% identity with variable light chain CDR1, CDR2 or CDR3 loop sequence as shown in SEQ ID NO:8 [8G7 Vl].

In a further preferred embodiment, the antibody comprises a sequence which shares at least 80% identity with heavy and/or light chain sequences as shown in SEQ ID NO:7 and SEQ ID NO:8 respectively, wherein the antibody reduces or inhibits the binding of C5a to C5aR.

In preferred embodiments of the present invention, the antibody is reactive with the second extracellular loop (residues 175 to 206) of human C5aR.

In further preferred embodiments, the antibody is reactive with an epitope comprising residues 179-184 (EEYFPP; SEQ ID NO: 27) of human C5aR.

In a further preferred embodiment of the present invention, the antibody the antibody is a monoclonal, recombinant antibody, chimeric or humanized antibody.

The antibody may be of any isotype. In a further preferred embodiment of the present invention, however, the antibody is a class IgG2a or class IgG3 antibody.

In another preferred embodiment of the invention, the antibody is a monoclonal antibody selected from the group consisting of MAb 3C5, MAb 8G7, and MAb 7H3.

The present invention also provides a hybridoma as deposited with ECACC under accession number 06081801.

The present invention also provides a hybridoma as deposited with ECACC under accession number 06081802.

The present invention also provides a hybridoma as deposited with ECACC under accession number 06081803.

It will be appreciated that various chemical derivatives of the antibodies of the invention may also be produced. For example, immunoconjugates consisting of an antibody of the present invention bound to a label such as a radioisotope or other tracer molecule can be made by techniques known in the art. Alternatively, the antibody may be bound to a therapeutically useful molecule which is targeted to its desired site of action by virtue of the antibody's binding specificity.

Accordingly, the present invention also provides a conjugate comprising an antibody of the present invention and a therapeutic agent.

It will be appreciated that a range of therapeutic agents may be used in the context of the present invention. Preferred therapeutic agents include agents that mediate cell death or protein inactivation. The therapeutic agent may be any of a large number of toxins known in the art. The toxin may be *Pseudomonas* exotoxin or a derivative thereof. In a preferred embodiment, the toxin is PE40.

The present invention also provides a conjugate comprising an antibody of the present invention and a detectable label.

The detectable label may be any suitable label known in the art. For example, the label may be a radiolabel, a fluorescent label, an enzymatic label or contrast media.

The present invention also provides an isolated nucleic acid molecule, the nucleic acid molecule comprising a sequence encoding an antibody of the present invention.

The present invention also provides a composition comprising an antibody according to the present invention and a pharmaceutically acceptable carrier.

The present invention also provides an antibody of the present invention for use as a medicament.

The present invention also provides a method for diagnosing a disorder involving leukocyte or neutrophil migration in a subject, the method comprising contacting a sample obtained from the subject in vitro with a conjugate of the present invention, and detecting immunospecific binding between the conjugate and the sample.

The present invention also provides an antibody of the present invention for use in the preparation of a medicament for the treatment of a disorder involving leukocyte or neutrophil migration.

The present invention also provides an antibody of the present invention for use in the preparation of a medicament for the treatment of an immunopathological disease.

In a preferred embodiment of the present invention, the C5aR is human C5aR.

The present invention also provides a method for inhibiting the interaction of a cell bearing C5aR with a ligand thereof, the method comprising exposing the cell to an antibody of the present invention.

The present invention also provides a method for inhibiting C5aR activity in a cell, the method comprising exposing the cell to an antibody of the present invention.

The present invention also provides a method of treating a disorder involving neutrophil migration in a subject, the method comprising administering to the subject an antibody of the present invention.

It will be appreciated by those skilled in the art that the antibodies of the present invention may also be used to detect, quantitate and/or localise cells expressing C5aR.

Accordingly, the present invention also provides a method for diagnosing a disorder involving neutrophil migration in a subject, the method comprising contacting a sample obtained from the subject with a conjugate of the present invention, and detecting immunospecific binding between the conjugate and the sample.

A variety of immunoassays may be used in the methods of diagnosis. Such immunoassays include competitive and non-competitive assay systems using techniques such as radioimmunoassays, ELISA, "sandwich" immunoassays, precipitin reactions, gel diffusion precipitin reactions, immunodiffusion assays, agglutination assays, complement fixation assays, immunoradiometric assays, fluorescent immunoassays and the like. Both in vitro and in vivo assays can be used.

The sample obtained from the subject may comprise any bodily fluid, such as peripheral blood, plasma, lymphatic fluid, peritoneal fluid, cerebrospinal fluid, or pleural fluid, or any body tissue. In vitro binding may be performed using histological specimens or subtractions of tissue or fluid. In vivo binding may be achieved by administering the conjugate by any means known in the art (such as intravenous, intraperitoneal, intrasarterial, etc.) such that immunospecific binding may be detected.

In addition, imaging techniques may be used, in which an antibody of the present invention is bound to a suitable imaging label. The labeled antibody may be administered in vivo to determine the localisation of C5aR in a subject.

Accordingly, the present invention also provides a method for diagnosing a disorder involving neutrophil migration in a subject, the method comprising administering to the subject an antibody of the present invention labeled with an imaging agent under conditions so as to form a complex between the antibody and cells presenting C5aR in the subject, and imaging the complex.

In one preferred embodiment of the present invention, the a disorder involving neutrophil migration is a C5aR mediated disorder. Preferably, the disorder is an immunopathological disorder.

The present invention also provides a method for delivering a therapeutic agent to a site of inflammation in a subject, the method comprising administering to the subject a conjugate of the present invention.

The present invention also provides a method for introducing genetic material into cells presenting C5aR, the method comprising contacting the cells with an antibody of the present invention, wherein the antibody is attached to or associated with genetic material.

In a preferred embodiment, cells presenting C5aR are selected from the group consisting of granulocytes, leukocytes, such as monocytes, macrophages, basophils and eosinophils, mast cells and lymphocytes including T cells, dendritic cells, and non-myeloid cells such as endothelial cells and smooth muscle cells.

Also encompassed by the present invention are methods of identifying additional ligands or other substances which bind C5aR, including inhibitors and/or promoters of mammalian C5aR function. For example, agents having the same or a similar binding specificity as that of an antibody of the present invention or functional fragment thereof can be identified by a competition assay with said antibody or fragment. Thus, the present invention also encompasses methods of identifying ligands or other substances which bind C5aR, including inhibitors (e.g., antagonists) or promoters (e.g., agonists) of receptor function. In one embodiment, cells which naturally express C5aR or suitable host cells which have been engineered to express C5aR or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

The following drawings are presented for the purpose of illustration only, and are not intended to be limiting.

BRIEF DESCRIPTION OF THE DRAWINGS

FIG. 8. Relative binding of C5aR-specific mAbs to the chimeric human/mouse C5aR receptors. Chimeric receptors are shown schematically (regions derived from hC5aR are shown in red and from mC5aR in black). The origin of the four extracellular domains is designated by 4-letter code (HHHH is wild-type human C5aR, mHHH has mouse N-terminal extracellular domain and human first, second, and third extracellular loops, etc). Transiently transfected L1.2 cells expressing chimeric receptors were stained with the various anti-C5aR mAbs. All anti-hC5aR mAbs showed distinct, domain-restricted binding profiles, binding either to receptors containing the human C5aR N-terminus or the 2nd extracellular loop. The anti-mouse C5aR mAb 20/70 binds to chimeric receptors containing the mouse C5aR 2nd extracellular loop.

Figure 11:
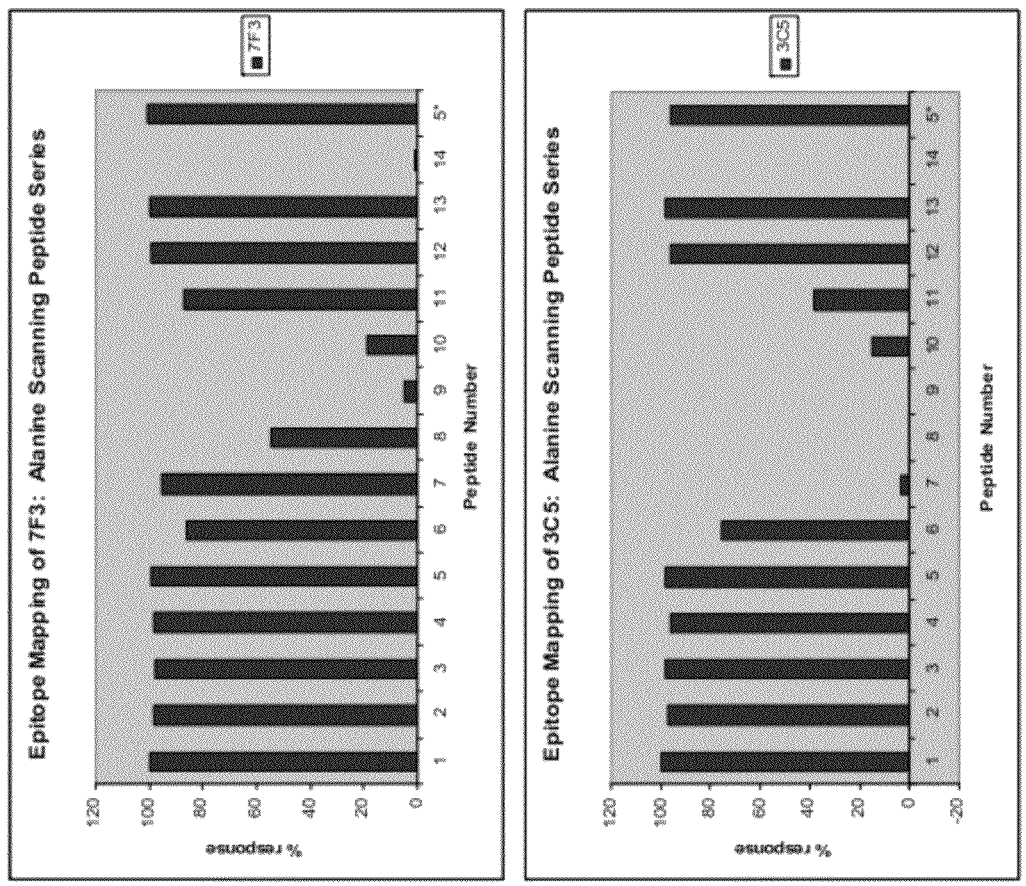
Figure 11:
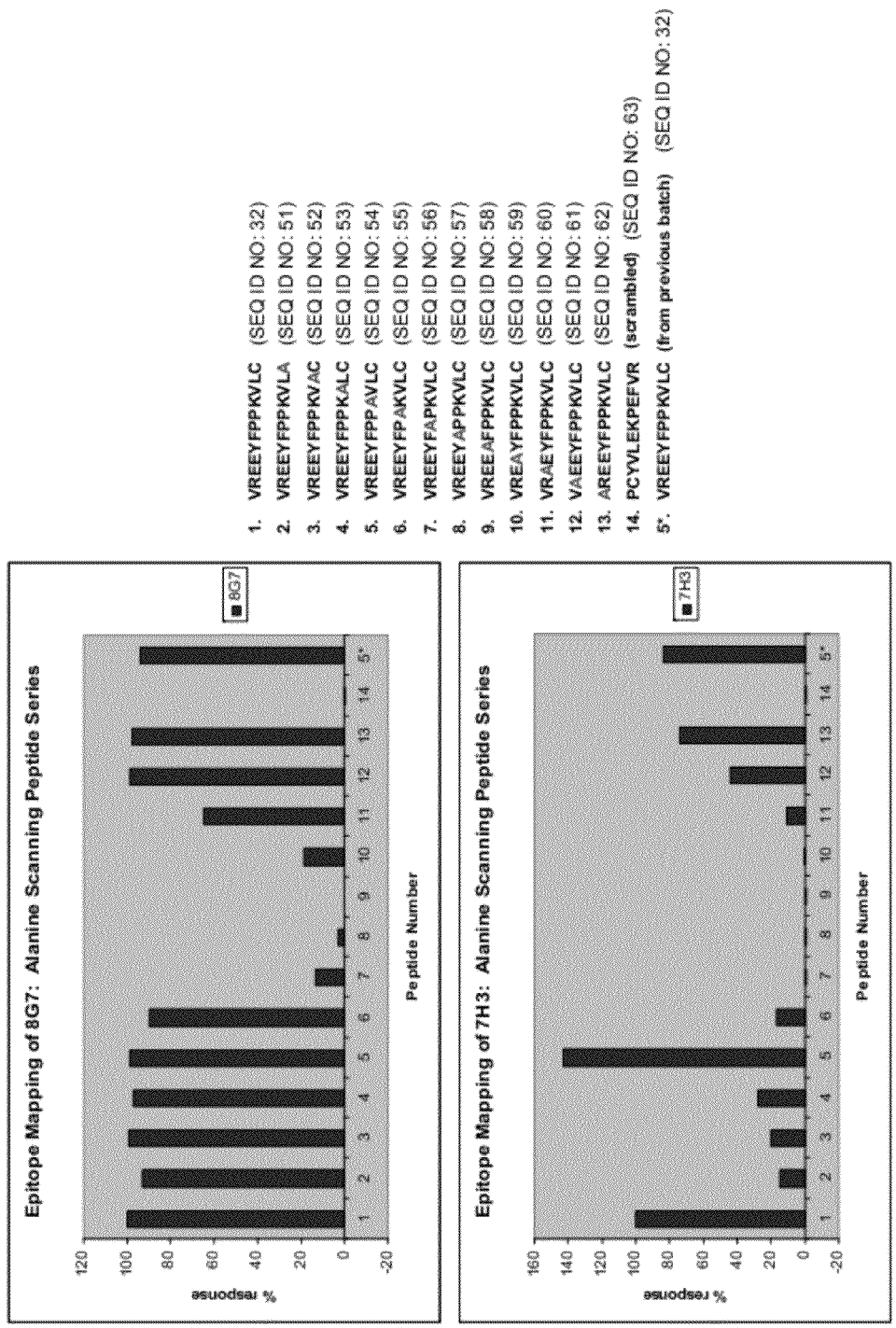

FIG. 11. (a). Mapping antibody contact residues using alanine mutants of 12-mer peptides identified the critical residues on hC5aR recognized by mAbs 7F3 and 3C5. (b). Mapping antibody contact residues using alanine mutants of 12-mer peptides identified the critical residues on hC5aR recognized by mAbs 8G7 and 7H3.

Figure 12:
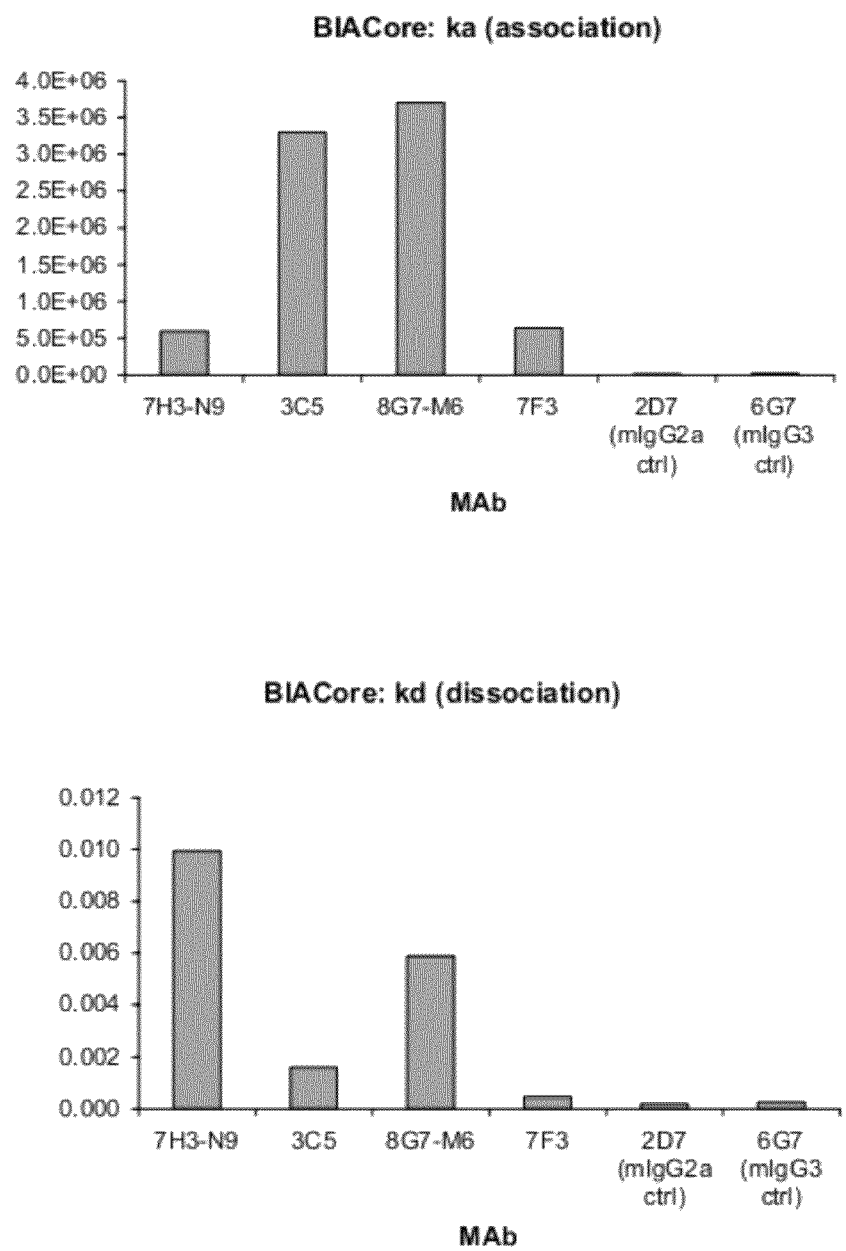
Figure 12:
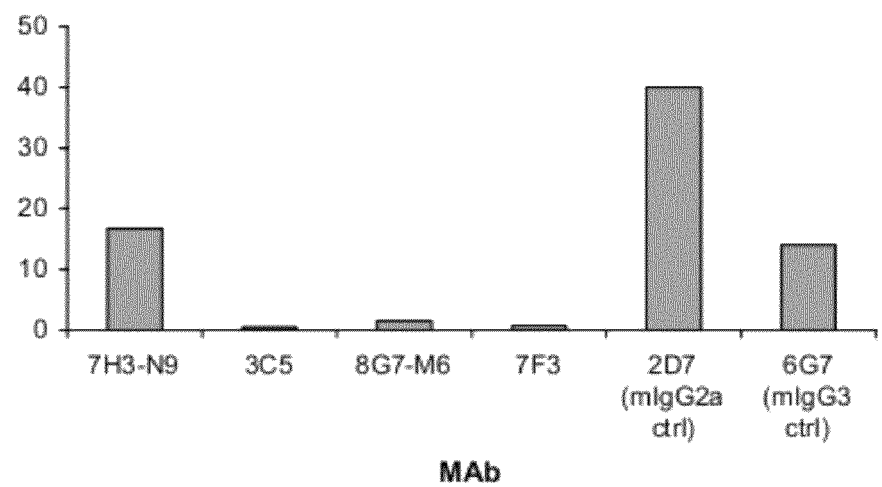

FIG. 12. Association and dissociation rates and binding affinities of mAbs 7F3, 3C5, 8G7 and 7H3 for peptide 23 in Biacore assay.

Figure 13:
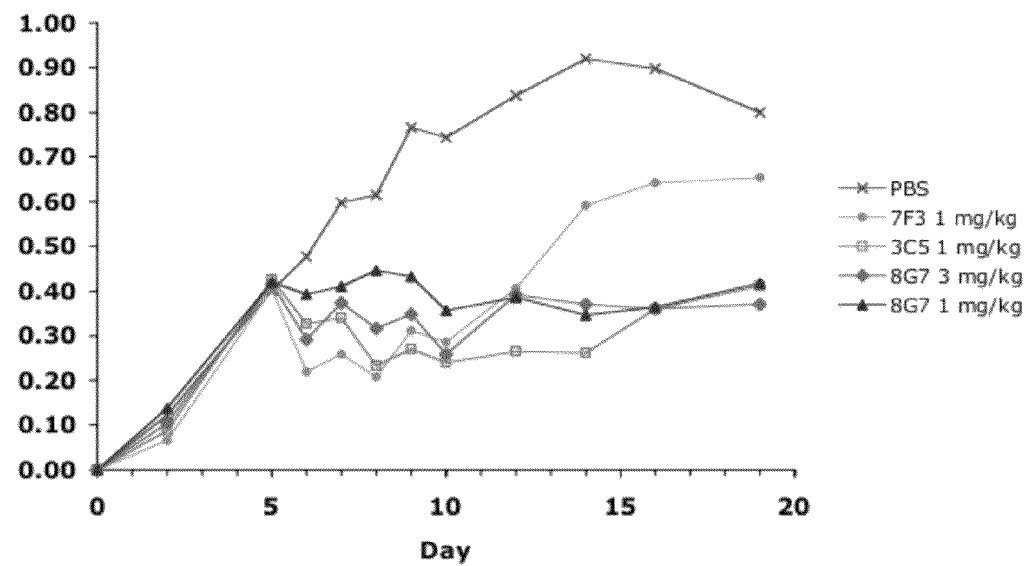

FIG. 13. Comparison of therapeutic efficacy of anti-hC5aR mAbs. hC5R1$^{+/+}$ mice were injected i.p. with 7F3, 3C5 or 8G7 (at 1 mg/kg or 3 mg/kg in PBS) once, on day 5 after inflammation had developed. Control group received PBS. Graph shows changes in paw (ankle) size from day 0. Group average (n=5-7 per group).

Figure 14:
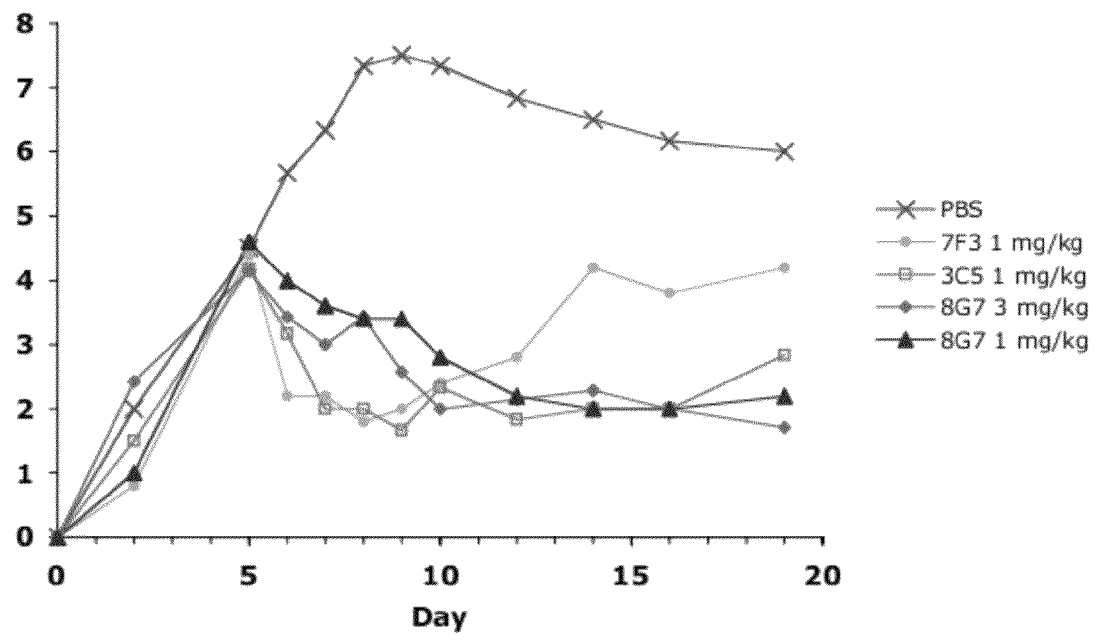

FIG. 14. Comparison of therapeutic efficacy of anti-hC5aR mAbs. hC5R1$^{+/+}$ mice were injected i.p. with 7F3, 3C5 or 8G7 (at 1 mg/kg or 3 mg/kg in PBS) once, on day 5 after inflammation had developed. Control group received PBS. Graph shows clinical scores. Group average (n=5-7 per group).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Key to Sequence Listings

SEQ ID NO:1 Human C5aR protein sequence
SEQ ID NO:2 Human C5aR peptide
SEQ ID NO:3 3C5 variable heavy chain (protein) sequence
SEQ ID NO:4 3C5 variable light chain (protein) sequence
SEQ ID NO:5 7H3 variable heavy chain (protein) sequence
SEQ ID NO:6 7H3 variable light chain (protein) sequence
SEQ ID NO:7 8G7 variable heavy chain (protein) sequence
SEQ ID NO:8 8G7 variable light chain (protein) sequence
SEQ ID NO:9 Modified human C5aR peptide
SEQ ID NOs: 10-25 Primers for construction of chimeric mouse/human C5aRs
SEQ ID NO:26 Biotinylated Human C5aR peptide (2nd extracellular loop)
SEQ ID NO:27 Residues 179 to 184 of human C5aR 2nd extracellular loop
SEQ ID NO:28-50 Overlapping 12 mer peptides from human C5aR 2nd extracellular loop containing the sequence EEYFPP (SEQ ID NO: 27)
SEQ ID NO:51-62 Alanine mutants of the peptide sequence VREEYFPPKVLC (SEQ ID NO: 32)
SEQ ID NO:63 Scrambled VREEYFPPKVLC (SEQ ID NO: 32) peptide C5aR Structure The amino acid sequence of human C5aR is provided in SEQ ID NO:1.

The various domains of human C5aR are defined as follows:

| | |
|---|---|
| amino acids 1-37 | extracellular domain - N-terminus |
| amino acids 38-61 | transmembrane domain |
| amino acids 62-71 | intracellular domain |
| amino acids 72-94 | transmembrane domain |
| amino acids 95-110 | extracellular domain - extracellular loop 1 |
| amino acids 111-132 | transmembrane domain |
| amino acids 133-149 | intracellular domain |
| amino acids 150-174 | transmembrane domain |
| amino acids 175-206 | extracellular domain - extracellular loop 2 |
| amino acids 207-227 | transmembrane domain |
| amino acids 228-242 | intracellular domain |
| amino acids 243-264 | transmembrane domain |
| amino acids 265-283 | extracellular domain - extracellular loop 3 |
| amino acids 284-307 | transmembrane domain |
| amino acids 308-350 | intracellular domain - C-terminus. |

Microorganism Deposit Details

The hybridoma which produces the monoclonal antibody designated 3C5 was deposited on 16 Aug. 2006 with European Collection of Cell Cultures (ECACC) at Porton down, Salisbury, Wiltshire, SP4 OJG, United Kingdom under accession number 06081801.

The hybridoma which produces the monoclonal antibody designated 7H3 was deposited on 16 Aug. 2006 with ECACC under accession number 06081802.

The hybridoma which produces the monoclonal antibody designated 8G7 was deposited on 16 Aug. 2006 with ECACC under accession number 06081803.

The hybridoma which produces the monoclonal antibody designated 7F3 was deposited on 6 Nov. 2000 with ECACC under accession number 00110609.

These deposits were made under the provisions of the Budapest Treaty on the International Recognition of the Deposit of Microorganisms for the Purpose of Patent Procedure and the Regulations thereunder. The deposits will be made available by ECACC under the terms of the Budapest Treaty. During the pendency of the above-referenced patent application, access to the deposit will be afforded by one determined by the Commissioner to be entitled thereto. All restrictions on the availability to the public of the cultures deposited will be irrevocably removed upon the granting of a patent on the above-identified application. However applicants retain the right to require requests for the deposits be made commensurate with 37 CFR §1.808(b). The deposits will be maintained for a period of 30 years after the date of deposit or 5 years after the last request for a sample or for the enforceable life of the patent, whichever is longer.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Antibodies

Antibodies of the present invention include polyclonal, monoclonal, humanized, bispecific, and heteroconjugate antibodies.

The term "antibody" as used in this invention includes intact molecules as well as fragments thereof, such as Fab, F(ab$^1$)$_2$, and Fv which are capable of binding the epitopic determinant. These antibody fragments retain some ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab$^1$, the fragment of an antibody molecule can be obtained by treating whole antibody with pepsin, followed by reduction, to yield an intact light chain and a portion of the heavy chain; two Fab$^1$ fragments are obtained per antibody molecule; (3) F(ab$^1$)$_2$, the fragment of the antibody that can be obtained by treating whole antibody with the enzyme pepsin without subsequent reduction; F(ab$^1$)$_2$ is a dimer of two Fab$^1$ fragments held together by two disulfide bonds; (4) Fv, defined as a genetically engineered fragment containing the variable region of the light chain and the variable region of the heavy chain expressed as two chains; (5) Single chain antibody ("SCA"), defined as a genetically engineered molecule containing the variable region of the light chain, the variable region of the heavy chain, linked by a suitable polypeptide linker as a genetically fused single chain molecule; and (6) Single domain antibody, typically a variable heavy domain devoid of a light chain.

Preferred antibodies of the present invention comprise variable regions or one or more CDR loops that are substantially the same as those of MAbs 3C5, 7H3 or 8G7.

The sequences of the variable regions for MAbs 3C5, 7H3 or 8G7 are set out in SEQ ID Nos:3 to 8. The CDR loops for each of these variable regions are defined as follows:

MAb 3C5
  CDR H1: residues 26-36 of SEQ ID NO:3 (inclusive);
  CDR H2: residues 51-66 of SEQ ID NO:3 (inclusive);
  CDR H3: residues 97-108 of SEQ ID NO:3 (inclusive);
  CDR L1: residues 24-39 of SEQ ID NO:4 (inclusive);
  CDR L2: residues 55-61 of SEQ ID NO:4 (inclusive);
  CDR L3: residues 94-102 of SEQ ID NO:4 (inclusive).
MAb 7H3
  CDR H1: residues 26-35 of SEQ ID NO:5 (inclusive);
  CDR H2: residues 50-68 of SEQ ID NO:5 (inclusive);
  CDR H3: residues 99-108 of SEQ ID NO:5 (inclusive);
  CDR L1: residues 24-39 of SEQ ID NO:6 (inclusive);
  CDR L2: residues 55-61 of SEQ ID NO:6 (inclusive);
  CDR L3: residues 94-102 of SEQ ID NO:6 (inclusive).
MAb 8G7
  CDR H1: residues 26-36 of SEQ ID NO:7 (inclusive);
  CDR H2: residues 51-66 of SEQ ID NO:7 (inclusive);
  CDR H3: residues 97-108 of SEQ ID NO:7 (inclusive);
  CDR L1: residues 24-39 of SEQ ID NO:8 (inclusive);
  CDR L2: residues 55-61 of SEQ ID NO:8 (inclusive);
  CDR L3: residues 94-102 of SEQ ID NO:8 (inclusive)

The L1, L2, L3 & H2 CDRs are as defined by Kabat. The limits of the H1 & H3 CDRs are modified from the Kabat definition and include additional residues at their N-terminal end. CDR H1 is extended to include the residues defined by Chothia as being part of CDR-H1. CDR H3 is extended to include 2 "contact" residues. Kabat numbering, defining CDRs and contact residues between Ab and antigen are known in the art.

It is interesting to note that the CDR loops of MAbs 3C5 and 8G7 share the following level of sequence identity:

| % identiy | CDR1 | CDR2 | CDR3 |
|---|---|---|---|
| 3C5 vs 8G7 | 10/11 91% | 13/16 81% | 10/12 83% |

It will be understood that the variable regions or CDR loops shown in the sequence listings may be modified for use in the present invention. Typically, modifications are made that maintain the binding specificity of the sequence. Conservative substitutions may be made, for example, without affecting the binding specificity of the antibody. The present invention encompasses antibodies comprising at least one CDR loop which has at least 80%, more preferably at least 85%, more preferably at least 90%, more preferably at least 95%, more preferably at least 98%, identity with a CDR loop within any one of SEQ ID NOS:3 to 8. For example, 1, 2, 3 or 4 amino acid substitutions may be made within the CDR loop, provided that the modified sequence retains substantially the same binding specificity.

In an alternative embodiment, modifications to the amino acid sequences of an antibody of the invention may be made intentionally to reduce the biological activity of the antibody. For example modified antibodies that remain capable of binding to C5aR but lack functional effector domains may be useful as inhibitors of the biological activity of C5aR.

Amino acid substitutions may also include the use of non-naturally occurring analogues, for example to increase blood plasma half-life of a therapeutically administered antibody.

In general, preferably less than 20%, 10% or 5% of the amino acid residues of a variant or derivative are altered as compared with the corresponding variable regions or CDR loops depicted in the sequence listings.

In the context of the present invention, a sequence "substantially the same" as one of the variable regions shown is the sequence listing may include an amino acid sequence which is at least 80%, 85%, or 90% identical, preferably at least 95 or 98% identical at the amino acid level over at least 20, preferably at least 50 amino acids with that variable region. Homology should typically be considered with respect to those regions of the sequence known to be essential for binding specificity rather than non-essential neighbouring sequences.

Homology comparisons can be conducted by eye, or more usually, with the aid of readily available sequence comparison programs. These commercially available computer programs can calculate % homology between two or more sequences.

Percentage homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

Most alignment programs allow the gap penalties to be modified. However, it is preferred to use the default values when using such software for sequence comparisons. For example when using the GCG Wisconsin Bestfit package (see below) the default gap penalty for amino acid sequences is –12 for a gap and –4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux, et al. *Nucl. Acids Res.* 12:387 (1984)). Examples of other software than can perform sequence comparisons include, but are not limited to, the BLAST package (see, Ausubel, et al., 1999 ibid—Chapter 18), FASTA (Atschul, et al. *J. Mol. Biol.* 403-410 (1990)) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Polyclonal Antibodies

An antibody of the present invention may be a polyclonal antibody. Methods of preparing polyclonal antibodies are known to the skilled artisan. Polyclonal antibodies can be raised in a mammal, for example, by one or more injections of the cells expressing the polypeptide of the first species derived from the transgenic mammal and, if desired, an adjuvant. Typically, the cells and/or adjuvant will be injected in the mammal by multiple subcutaneous or intraperitoneal injections. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies

The antibodies produced by the method of the invention may, alternatively, be monoclonal antibodies. Monoclonal antibodies may be prepared using hybridoma methods, such as those described by Kohler, et al. *Nature* 256:495 (1975). In a hybridoma method, a mouse, hamster, or other appropriate host animal, is typically immunized with the cells expressing the polypeptide of the first species derived from the transgenic mammal to elicit lymphocytes that produce or are capable of producing antibodies that will specifically bind to the polypeptide of the first species.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies (Kozbor, *Immunol.,* 133:3001 (1984); Brodeur, et al. *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against the polypeptide of the first species. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson, et al. *Anal. Biochem.* 107:220 (1980).

After the desired hybridoma cells are identified, the clones maybe subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Human and Humanized Antibodies

The antibodies of the present invention may be humanized antibodies or human antibodies. Humanized forms of non-human (e.g., murine) antibodies are chimeric immunoglobulins, immunoglobulin chains or fragments thereof (such as Fv, Fab, Fab$^1$, F(ab$^1$)$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al. *Nature* 321:522-525 (1986); Riechmann, et al. *Nature* 332:323-329 (1988); and Presta, *Curr. Op. Struct. Biol.*, 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones, et al. *Nature* 321:522-525 (1986); Riechmann, et al. *Nature* 332:323-327 (1988); Verhoeyen, et al. *Science* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom, et al. *J. Mol. Biol.* 227:381 (1991); Marks, et al. *J. Mol. Biol.* 222:581 (1991)). The techniques of Cole, et al. are also available for the preparation of human monoclonal antibodies (Cole, et al. *Monoclonal Antibodies and Cancer Therapy*, Alan R. Liss, p. 77 (1985) and Boerner, et al. *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807, 5,545,806, 5,569,825, 5,625,126, 5,633,425, and 5,661,016, and in the following scientific publications: Marks, et al. *Bio/Technology* 10:779-783 (1992); Lonberg, et al. *Nature* 368:856-859 (1994); Morrison, *Nature* 368:812-13 (1994); Fishwild, et al. *Nature Biotechnol.* 14:845-51 (1996); Neuberger, *Nature Biotechnol.* 14:826 (1996); Lonberg, et al. *Intern. Rev. Immunol.* 13:65-93 (1995).

The antibodies may also be affinity matured using known selection and/or mutagenesis methods as are known in the art. Preferred affinity matured antibodies have an affinity which is five times, more preferably 10 times, even more preferably 20 or 30 times greater than the starting antibody (generally murine, humanized or human) from which the matured antibody is prepared.

Bispecific Antibodies

Bispecific antibodies are monoclonal, preferably human or humanized, antibodies that have binding specificities for at least two different antigens. For example, one of the binding specificities may be for C5aR, the other one may be for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein, et al. *Nature* 305:537-539 (1983)). Because of the random assortment of immunoglobulin heavy and light chains, these hybridomas (quadromas) produce a potential mixture often different antibody molecules, of which only one has the correct bispecific structure. The purification of the correct molecule is usually accomplished by affinity chromatography steps. Similar procedures are disclosed in WO 93/08829, published 13 May 1993, and in Traunecker, et al, *Embo. J.* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh, et al. *Meth. in Enzymol.* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan, et al. *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby, et al. *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers (Kostelny, et al. *J. Immunol.* 148(5):1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger, et al. *Proc. Natl. Acad. Sci. USA* 90:6444-6448 (1993) has provided an alternative mechanism for making bispecific antibody fragments. The fragments comprise a heavy-chain variable domain (V H) connected to a light-chain variable domain (V L) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported (see, Gruber, et al. *J. Immunol.* 152.5368 (1994)).

Antibodies with more than two valencies are contemplated. For example, trispecific antibodies can be prepared (Tutt, et al. *J. Immunol.* 147:60 (1991)).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC) (see Caron, et al. *J. Exp Med.* 176:1191-1195 (1992); Shopes, *Immunol.* 148:2918-2922 (1992)). Homodimeric antibodies with enhanced anti-tumor activity may also be prepared using heterobifunctional cross-linkers as described in Wolff, et al. *Canc. Res.* 53:2560-2565 (1993). Alternatively, an antibody can be engineered that has dual Fc regions and may thereby have enhanced complement lysis and ADCC capabilities (see Stevenson, et al. *Anti-Cancer Drug Design* 3:219-230 (1989)).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radio conjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta, et al. *Science* 238:1098 (1987). $^{14}$C-labeled 1-isothiocyanatobenzyl-3-methyldiethylene triaminepentaacetic acid (MX-DTPA) is an exemplary chelating agent for conjugation of radionucleotide to the antibody (see WO 94/11026).

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Antibody Isotypes

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared secondarily, from a parental hybridoma secreting monoclonal antibody of different isotype, by using the sib selection technique to isolate class-switch variants (Steplewski, et al. *Proc. Natl. Acad. Sci. U.S.A.* 82:8653 (1985); Spira, et al. *J. Immunol. Methods* 74:307 (1984)).

Binding Characteristics

In one embodiment of the invention, the antibody is defined in terms of its inhibitory concentration 50% value.

The term "inhibitory concentration 50%" (abbreviated as "$IC_{50}$") represents the concentration of an inhibitor (e.g., an antibody of the invention) that is required for 50% inhibition of a given activity of the molecule the inhibitor targets (e.g. binding of C5a to C5aR or a fragment thereof). It will be understood by one in the art that a lower $IC_{50}$ value corresponds to a more potent inhibitor.

In one embodiment, the antibody of the invention inhibits C5a binding to C5aR with an $IC_{50}$ value that is at least 1.5 fold lower than that of MAb7F3 when determined under identical conditions.

In another embodiment, the antibody of the invention inhibits C5a binding to C5aR with an $IC_{50}$ of less than 500 pM, more preferably less than 400 pM, more preferably less than 300 pM, and less than 200 pM. Preferably, these $IC_{50}$ values are determined by binding assays conducted using human neutrophils as described in the Examples herein.

Another embodiment of present invention relates to antibodies that bind C5aR or a fragment thereof with a $K_d$ (affinity constant) that is at least 1.3 fold lower, preferably 1.4 fold lower than that of MAb7F3 when determined under identical conditions.

In another embodiment, the antibody of the invention binds to C5aR or a fragment thereof with a $K_d$ of less than 1.4 nM, more preferably less than 0.7 nM, more preferably less than 0.5 nM, more preferably less than 0.3 nM.

Another embodiment of present invention relates to antibodies that bind C5aR or a fragment thereof with an association constant or $k_a$ rate that is at least 1.5 fold higher than that of MAb7F3 when determined under identical conditions.

In another embodiment, the antibody of the invention binds to C5aR or a fragment thereof with an association constant or $k_a$ rate of at least $6.8 \times 10^5$ $M^{-1}s^{-1}$, more preferably at least $10^6$ $M^{-1}s^{-1}$, preferably at least $3 \times 10^6$ $M^{-1}s^{-1}$.

In a preferred embodiment the binding affinity is determined by BIACore analysis of binding of the antibody to a peptide derived from human C5aR. Preferably the peptide derived from human C5aR comprises the sequence LYRVVREEYFPPKVLCGVDYSHDKRRERAVAIV (SEQ ID NO:2). More preferably, the binding analysis is conducted by BIACore binding assays under the conditions described in the examples herein.

In Vitro Assays

The monoclonal antibodies of the invention are suited for use in vitro, for example, in immunoassays in which they can be utilized in liquid phase or bound to a solid phase carrier. The antibodies may be useful for monitoring the level of C5aR in a sample. Similarly, anti-idiotype antibodies are useful for measuring the level of C5a in a sample. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of C5aR. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

In one embodiment, cells which naturally express C5aR or cells comprising a recombinant nucleic acid sequence which encodes a C5aR or variant thereof are used in binding assays of the present invention. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

Binding inhibition assays can also be used to identify antibodies or fragments thereof which bind C5aR and inhibit binding of C5a to C5aR or a functional variant. For example, a binding assay can be conducted in which a reduction in the binding of C5a (in the presence of the antibody), as compared to binding of C5a in the absence of the antibody, is detected or measured. A composition comprising an isolated and/or recombinant mammalian C5aR or functional variant thereof can be contacted with C5a and antibody simultaneously, or one after the other, in either order. A reduction in the extent of binding of the ligand in the presence of the antibody, is indicative of inhibition of binding by the antibody. For example, binding of the ligand could be decreased or abolished.

Other methods of identifying the presence of an antibody which binds C5aR are available, such as other suitable binding assays, or methods which monitor events which are triggered by receptor binding, including signaling function and/or stimulation of a cellular response (e.g., leukocyte trafficking) Antibodies which are identified in this manner can be further assessed to determine whether, subsequent to binding, they act to inhibit other functions of C5aR and/or to assess their therapeutic utility.

Signaling Assays

The binding of a ligand or promoter, such as an agonist, to C5aR can result in signaling by this G protein-coupled receptor, and the activity of G proteins as well as other intracellular signaling molecules is stimulated. The induction of signaling function by a compound (e.g., an antibody or fragment thereof) can be monitored using any suitable method. Such an assay can be used to identify antibody agonists of C5aR. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium can be assayed by methods known in the art or other suitable methods (see, for example, Neote, et al. *Cell* 72: 415-425, 1993; Van Riper, et al. *J. Exp. Med.* 177:851-856, 1993; Dahinden, et al. *J. Exp. Med.* 179:751-756, 1994).

For example, the functional assay of Sledziewski, et al. using hybrid G protein coupled receptors can be used to monitor the ability of a ligand or promoter to bind receptor and activate a G protein (Sledziewski, et al. U.S. Pat. No. 5,284,746).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to C5aR and/or inhibit function associated with binding of the ligand to the receptor. These assays are based on the functional migration of cells in vitro or in vivo induced by a compound. Chemotaxis can be assessed by any suitable means, for example, in an assay utilizing a 96-well chemotaxis plate, or using other art-recognized methods for assessing chemotaxis. For example, the use of an in vitro transendothelial chemotaxis assay is described by Springer, et al. (Springer, et al. WO 94/20142, published Sep. 15, 1994; see also Berman, et al. *Immunol. Invest.* 17:625-677 (1988)). Migration across endothelium into collagen gels has also been described (Kavanaugh, et al. *J. Immunol.* 146:4149-4156 (1991)). Stable transfectants of mouse L1-2 pre-B cells or of other suitable host cells capable of chemotaxis may be used in chemotaxis assays.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-I, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody). In one embodiment, particularly for T cells, monocytes or cells expressing C5aR, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing C5aR can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing C5aR in this assay are inhibitors of receptor function (e.g., inhibitors of stimulatory function). A reduction in the extent of migration induced by the ligand or promoter in the presence of the antibody or fragment is indicative of inhibitory activity. Separate binding studies could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see "*Models of Inflammation*"). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of C5aR can be assessed by monitoring cellular responses induced by active receptor, using suitable host cells containing receptor.
Identification of Additional Ligands, Inhibitors and/or Promoters of C5aR The assays described above, which can be used to assess binding and function of the antibodies and fragments of the present invention, can be adapted to identify additional ligands or other substances which bind C5aR or functional variant thereof, as well as inhibitors and/or promoters of C5aR function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind C5aR, as well as inhibitors (e.g., antagonists) or promoters (e.g., agonists) of receptor function. In one embodiment, cells bearing a C5aR protein or functional variant thereof (e.g., leukocytes, cell lines or suitable host cells which have been engineered to express a mammalian C5aR protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Antagonists of receptor function can be used to inhibit (reduce or prevent) receptor activity, and ligands and/or agonists can be used to induce (trigger or enhance) normal receptor function where indicated. Thus, the present invention provides a method of treating inflammatory diseases, including autoimmune disease and graft rejection, comprising administering an antagonist of receptor function to an individual (e.g., a mammal). The present invention further provides a method of stimulating receptor function by administering a novel ligand or agonist of receptor function to an individual, providing a new approach to selective stimulation of leukocyte function, which is useful, for example, in the treatment of infectious diseases and cancer.

As used herein, a "ligand" of a C5aR protein refers to a particular class of substances which bind to a mammalian C5aR protein, including natural ligands and synthetic and/or recombinant forms of natural ligands. In a preferred embodiment, ligand binding of a C5aR protein occurs with high affinity.

As used herein, an "antagonist" is a substance which inhibits (decreases or prevents) at least one function characteristic of a C5aR protein such as a binding activity (e.g., ligand binding, promoter binding, antibody binding), a signaling activity (e.g., activation of a mammalian G protein, induction of rapid and transient increase in the concentration of cytosolic free calcium) and/or cellular response function (e.g., stimulation of chemotaxis, exocytosis or inflammatory mediator release by leukocytes).

The term "antagonist" encompasses substances which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, an "agonist" is a substance which promotes (induces, causes, enhances or increases) at least one function characteristic of a C5aR protein such as a binding activity (e.g., ligand, inhibitor and/or promoter binding), a signaling activity (e.g., activation of a mammalian G protein, induction of rapid and transient increase in the concentration of cytosolic free calcium) and/or a cellular response function (e.g., stimulation of chemotaxis, exocytosis or inflammatory mediator release by leukocytes).

The term agonist encompasses substances which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds C5aR or ligand binding variant thereof, including ligands, antagonists, agonists, and other substances which bind C5aR or functional variant. According to the method, an agent to be tested, an antibody or antigen-binding fragment of the present invention (e.g. an antibody having an epitopic specificity which is the same as or similar to that of 7F3, and antigen-binding fragments thereof) and a composition comprising a C5aR or a ligand binding variant thereof can be combined. The foregoing components are combined under conditions suitable for binding of the antibody or antigen-binding fragment to C5aR, and binding of the antibody or fragment to the C5aR is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising C5aR can be a membrane fraction of a cell bearing recombinant C5aR protein or ligand binding variant thereof. The antibody or fragment thereof can be labeled with a label such as a radioisotope, spin label, antigen or epitope label, enzyme label, fluorescent group and chemiluminescent group.

There are reasons why displacement of anti-C5aR mAb may identify C5a receptor antagonists more easily. Binding of C5a to C5aR is a two step process involving different regions of C5aR (see Klco, et al. *Nat. Struct. Mol. Biol.* 12:320-326 (2005)), whereas anti-C5aR monoclonal antibodies i.e. 7F3 or 3C5 recognise the single critical region for inhibition in the second extracellular loop.
Models of Inflammation In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with C5aR into a suitable animal, such as rabbit, mouse, rat, guinea pig or rhesus macaque can be monitored (see e.g., Van Damme, et al. *J. Exp. Med.* 176:59-65 (1992); Zachariae, et al. *J. Exp. Med.* 171:2177-2182 (1990); Jose, et al. *J. Exp. Med.* 179:881-887 (1994)). In one embodiment, skin biopsies are assessed histologically for infiltration of leukocytes (e.g., eosinophils, granulocytes). In another embodiment, labeled cells (e.g., stably transfected cells expressing C5aR) capable of chemotaxis and extravasation are administered to the animal. An antibody or fragment to be assessed can be administered, either before, simultaneously with or after the labeled cells are administered to the test animal. A decrease of the extent of infiltration in the presence of antibody as compared with the extent of infiltration in the absence of inhibitor is indicative of inhibition.

Uses

The antibodies of the present invention are useful in a variety of applications, including research, diagnostic and therapeutic applications.

C5aR has an important role in leukocyte trafficking Thus, C5aR is a chemoattractant receptor for neutrophil, eosinophil, T cell or T cell subset or monocyte migration to certain inflammatory sites, and so anti-C5aR antibodies can be used to inhibit (reduce or prevent) leukocyte migration, particularly that associated with neutrophil tissue injury such as reperfusion injury and stroke, T cell dysfunction, such as autoimmune disease, or allergic reactions or with monocyte-mediated disorders such as atherosclerosis.

The antibodies described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand).

Thus, the present invention provides a method of inhibiting leukocyte trafficking in a mammal (e.g., a human patient), comprising administering to the mammal an effective amount of an antibody of the present invention. The present invention also provides a method of inhibiting other effects associated with C5aR activity such as histamine release from basophils and granule release from eosinophils, basophils and neutrophils. Administration of an antibody of the present invention can result in amelioration or elimination of the disease state.

The monoclonal antibodies can also be used immunotherapeutically for immunopathological associated disease. The term "immunotherapeutically" or "immunotherapy" as used herein in conjunction with the antibodies of the invention denotes both prophylactic as well as therapeutic administration. Thus, the antibodies can be administered to high-risk patients in order to lessen the likelihood and/or severity of immunopathological disease or administered to patients already evidencing active disease, for example sepsis due to gram-negative bacterial infection.

The antibodies can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, allograft rejection, fibrotic disease, asthma, inflammatory glomerulopathies or any immune complex related disorder.

Diseases or conditions of humans or other species which can be treated with antibodies of the invention include, but are not limited to: (a) inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); (b) autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease; (c) graft rejection (e.g., in transplantation), including allograft rejection or graft-versus-host disease; (d) atherosclerosis; (e) cancers with leukocyte infiltration of the skin or organs; (f) other diseases or conditions (including C5aR-mediated diseases or conditions), in which undesirable inflammatory responses are to be inhibited can be treated, including, but not limited to, reperfusion injury, stroke, adult respiratory distress syndrome, certain hematologic malignancies, cytokine-induced toxicity (e.g., septic shock, endotoxic shock), polymyositis, dermatomyositis, pemphigoid, Alzheimers Disease and granulomatous diseases including sarcoidosis, hemophilic synovitis and age-related macular degeneration.

Anti-C5aR antibodies of the present invention can block the binding of one or more ligands, thereby blocking the downstream cascade of one or more events leading to the above disorders.

In a preferred embodiment, the antibodies of the present invention are used in the treatment of sepsis, stroke or adult respiratory distress syndrome.

In another embodiment, the various antibodies of the present invention can be used to detect C5aR or to measure the expression of receptor, for example, on leukocytes (e.g. neutrophils, monocytes, B cells), endothelial cells and/or on cells transfected with a receptor gene. Thus, they also have utility in applications such as cell sorting (e.g., flow cytometry, fluorescence activated cell sorting), for diagnostic or research purposes.

The anti-C5aR antibodies of the present invention have value in diagnostic applications. Typically, diagnostic assays entail detecting the formation of a complex resulting from the binding of an antibody or fragment thereof to C5aR. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827, 3,850,752, 3,901,654, and 4,098,876). Immunohistochemistry of tissue samples may also be used in the diagnostic methods of the present invention. When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

Kits for use in detecting the presence of a C5aR protein in a biological sample can also be prepared. Such kits will include an antibody or functional fragment thereof which binds to C5aR, as well as one or more ancillary reagents suitable for detecting the presence of a complex between the antibody or fragment and C5aR. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of C5aR by a cell, in which a composition comprising a cell or fraction thereof (e.g., membrane fraction) is contacted with an antibody of the invention under conditions appropriate for binding of the antibody or fragment thereto, and binding is monitored. Detection of the antibody, indicative of the formation of a complex between antibody and C5aR, indicates the presence of the receptor. Binding of antibody to the cell can be determined using techniques such as those described in WO 03/062278. The method can be used to detect expression of C5aR on cells from an individual (e.g., in a sample, such as a body fluid, such as blood, saliva or other suitable sample). The level of expression of C5aR on the surface of T cells or monocytes can also be determined, for instance, by flow cytometry, and the level of expression (e.g., staining intensity) can be correlated with disease susceptibility, progression or risk.

Modes of Administration

A variety of routes of administration are possible including, but not necessarily limited to, oral, dietary, topical, parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody to be administered will vary according to the route of administration and formulation (e.g., solution, emulsion, capsule) selected. An appropriate pharmaceutical composition comprising an antibody to be administered can be prepared in a physiologically acceptable vehicle or carrier. A mixture of antibodies can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The dosage ranges for the administration of the antibodies of the invention are those large enough to produce the desired effect in which the symptoms of the immunopathological disease are ameliorated or the likelihood of infection or over stimulation of the immune system decreased. The dosage should not be so large as to cause adverse side effects, such as hyper-viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

One or more antibodies of the present invention can be administered to an individual by an appropriate route, either alone or in combination with (before, simultaneous with, or after) another drug or agent. For example, the antibodies of the present invention can also be used in combination with other monoclonal or polyclonal antibodies (e.g., in combination with antibodies which bind chemokine receptors, including, but not limited to, CCR2 and CCR3) or with anti-TNF or other anti-inflammatory agents or with existing blood plasma products, such as commercially available gamma globulin and immune globulin products used in prophylactic or therapeutic treatments. The antibodies of the present invention can be used as separately administered compositions given in conjunction with antibiotics and/or antimicrobial agents.

It will be appreciated by those skilled in the art that the antibodies of the present invention may be introduced into a subject by administering a nucleic acid molecule comprising a sequence encoding the antibody. The nucleic acid molecule may be in the form of DNA or RNA or a chimeric molecule comprising both DNA or RNA. A nucleotide sequence encoding the antibody may be cloned into an expression vector where the sequence encoding the agent is operably linked with expression control elements. Expression control elements are well known in the art and include, for example, promoters, enhancers and appropriate start and stop codons.

A variety of methods can be used for introducing a nucleic acid encoding the antibody into a target cell in vivo. For example, the naked nucleic acid may be injected at the target site, may be encapsulated into liposomes, or may be introduced by way of a viral vector.

Direct injection of a nucleic acid molecule alone or encapsulated, for example, in cationic liposomes may be used for stable gene transfer of a nucleic acid encoding TSP-I into non-dividing or dividing cells in vivo (Ulmer et al. Science, 259:1745-1749 (1993)). In addition, the nucleic acid can be transferred into a variety of tissues in vivo using the particle bombardment method (Williams et al. *Proc. Natl. Acad. Sci. USA*, 88:2726-2730 (1991)).

Viral vectors are useful for gene transfer of a nucleic acid molecules encoding the antibody into a specific cell type in vivo. Viruses are specialized infectious agents that can infect and propagate in specific cell types. This specificity for infecting particular cell types is especially suitable for targeting the antibody to selected cells in vivo. The selection of a viral vector will depend, in part, on the cell type to be targeted.

Specialized viral vectors are well known in the art that can target to specific cell types. Such vectors include, for example, recombinant adeno-associated viral vectors having general or tissue-specific promoters (U.S. Pat. No. 5,354, 678). Recombinant adeno-associated viral vectors have the added advantage that the recombinant virus can stably integrate into the chromatin of even quiescent non-proliferating cells (Lebkowski et al. *Mol. and Cell. Biol.* 8(10):3988-3996 (1988)).

Viral vectors can be constructed to further control the type of cell that expresses the encoded antibody by incorporating a tissue-specific promoter or enhancer into the vector (Dai et al. *Proc. Natl. Acad. Sci. USA* 89:10892-10895 (1992)).

Retroviral vectors are also suitable for the methods for delivering nucleic acid molecules encoding the antibody in vivo. Such vectors can be constructed either to function as infectious particles or as non-infectious particles that undergo only a single initial round of infection.

Receptor-mediated DNA delivery approaches also can be used to deliver a nucleic acid molecule encoding the antibody into a cell in a tissue-specific manner using a tissue-specific ligand or an antibody that is non-covalently complexed with the nucleic acid molecule via a bridging molecule (Curiel et al. 1992; Wu et al. *J. Biol. Chem.* 262(10):4429-4432 (1987)).

Gene transfer to obtain expression of the antibody in a subject also can be performed by, for example, ex vivo transfection of autologous cells. Suitable cells for such ex vivo transfection include blood cells since these cells are readily accessible for manipulation and reintroduction back into the subject by methods well known in the art.

Gene transfer through transfection of cells ex vivo can be performed by a variety of methods, including, for example, calcium phosphate precipitation, diethylaminoethyl dextran, electroporation, lipofection, or viral infection. Such methods are well known in the art (see, for example, Sambrook, et al. *Molecular Cloning: A Laboratory Manual*, Cold Springs Harbour Laboratory Press (1989)). Once the cells are transfected, they are then transplanted or grafted back into a subject to be treated. The cells once introduced into the body can produce the antibody, which can enter the circulation and inhibit platelet aggregation at the site of the disease or condition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

The present invention will now be illustrated by the following Examples, which are not intended to be limiting in any way. The teachings of all references cited herein are incorporated herein by reference.

EXAMPLES

Experimental Details

Generation of Human C5aR Knock-in Mice

A knock-out/knock-in strategy was adopted to construct a transgenic mouse expressing human C5aR, but not mouse C5aR, under the control of the mouse C5aR gene promoter. The targeting vector comprised a 3.5 kb region of mouse C57BL/6 genomic DNA upstream of the C5aR gene exon 3, human C5aR gene exon 3 coding sequence, mouse C5aR gene 3' untranslated region, phosphoglucokinase promoter and neomycin resistance gene flanked by loxP sites and a 3 kb region of mouse genomic DNA downstream of the C5aR gene in the vector pLOz (Ozgene, Perth, Australia).

Genomic DNA fragments were generated using PCR amplification. The vector was transfected into C57BL/6 embryonic stem cells and DNA from G418 resistant colonies was screened by Southern blot. Xba I and EcoR V digested DNA was hybridized with 5' and 3' probe, respectively to identify clones with the correct homologous recombination event at both 5' and 3' ends. Chimeras generated from blastocysts injected with the correctly targeted ES clones were mated with C57BL/6 females. Germline transmission of the human C5aR gene was confirmed by Southern blot of mouse tail genomic DNA. Mice homozygous for the human C5aR gene ($hC5R1^{+/+}$) were generated and PCR, southern blot, and FACS staining confirmed the absence of mC5aR.

Neutrophil Isolation

Human neutrophils were isolated from the peripheral venous blood of healthy volunteers as previously described (Haslett, et al. Am. J. Pathol. 119:101-110 (1985)) with modification. Briefly, blood samples collected into EDTA-coated vacutainers were centrifuged at 400×g for 15 min and then the plasma and buffy coats were removed. Following 1% dextran sedimentation for 30 min, the white blood cells were pelleted by centrifugation at 300×g for 5 min and washed with PBS. The cells were then centrifuged at 500×g for 30 min on a cushion of 65% percoll (density, 1.093 g/ml, Amersham Bioscience). After centrifugation, the neutrophils were re-suspended in PBS. Mouse neutrophils were isolated from both hind leg femurs by forcing 5 ml DMEM (GIBCO) medium with 10% fetal calf serum through the bone with a syringe. Neutrophils were separated by density centrifugation over Ficoll-Paque® (Amersham Bioscience). Red blood cells were lysed by hypotonic buffer (155 mM $NH_4Cl$, 10 mM $KHCO_3$, 1 mM EDTA). Cell viability was determined by trypan blue exclusion and the neutrophil pellet was re-suspended in PBS.

Monoclonal antibody generation C57BL/6 mice were immunized with about $2 \times 10^7$ L1.2 transfectants expressing high levels of hC5aR (Campbell, et al. *J. Cell Biol.* 134:255-266 (1996)), i.p., 5 times at 2 week intervals then once i.v. Four days following the final i.v. immunization, the spleen was removed and the cells fused with the SP2/0 cell line using standard procedures. C57BL/6 mice were immunized with about $1 \times 10^7$ neutrophils isolated from femurs of $hC5R1^{+/+}$ mice in a similar fashion, twice i.v., once i.p. and a final i.v. immunization. Hybridomas were grown in DMEM (GIBCO) containing 10% Fetalclone® (HyClone) and HAT supplement (SIGMA) and culture supernatant was taken for initial screening. Production of selected antibodies was scaled up and mAb was purified by protein A or G chromatography, concentrated, buffer exchanged, and endotoxins removed. MAb concentration was determined using a mouse IgG ELISA kit (Roche).

Flow Cytometry

To assess reactivity of mAbs against transfected cells or leukocytes, we used indirect immunofluorescence staining and flow cytometry. Cells were washed once with PBS, and re-suspended in 100 µl PBS containing 2% human serum and 0.1% sodium azide (staining buffer), purified antibody, or 50 µl hybridoma culture supernatant. After 20 min at 4° C., cells were washed twice with staining buffer, and re-suspended in 50 µl FITC-conjugated affinity purified F(ab') goat anti-mouse IgG (Jackson ImmunoResearch Laboratories) diluted 1:200 in staining buffer. After incubating for 20 min at 4° C., cells were washed twice with staining buffer and analyzed on the FACSCalibur™ (Becton-Dickinson) to determine the level of surface expression. Propidium iodide staining was used to exclude dead cells.

Binding Assays

Human neutrophils were washed and re-suspended in binding buffer (50 mM HEPES, pH7.5, 1 mM CaCl2, 5 mM MgCl2, and 0.5% BSA) at $1 \times 10^7$/ml. For each binding reaction (in a final volume of 120 µl), 40 µl cell suspension ($4 \times 10^5$ cells) with an appropriate amount of anti-hC5aR mAb, isotype matched control mAb or unlabelled human C5a (SIGMA) was incubated at room temperature for 15 min. $^{125}$I-labelled human C5a (Perkin Elmer) was added at a final concentration of 0.4 nM and the reactions were incubated at room temperature for 60 min. Cells were then collected and washed 3 times with binding buffer containing 150 mM NaCl. Cells were then transferred to Opti plates (Perkin Elmer) with MicroScint 20 scintillation fluid and radioactivity counted on TopCount (Packard). Each sample was assayed in triplicate.

BIACore™ Analysis

1. Instrument reagents:
1.1 Hardware/Software: BIACore™ 2000BIACore™ 2000 control software
    Running buffer: HBS-EP (BIACore™, #BR-1001-88)
    Regeneration buffer: 100 mM HCl
    Sensor Chip Sensor Chip SA (streptavadin; BIACore #BR-1003-98)
    Biotinylated Human C5aR Peptide (2nd loop): Biotin-SGSGLYRVVREEYFPPKVLCGVDYSHD-KRRERAVAIV-OH (SEQ ID NO: 26).
2. Assay Procedure/Instrument Settings:
2.1 Flow rate of assay: 30 µl/min
2.2 Condition SA chip (FcI and Fc2) with 3×1-minute injections of IM NaCl in 50 mM NaOH.
2.3 Sample Preparation:
    Dilute antibody samples in HBS-EP (BIACore™, #BR-12001-88)
    Use the following concentrations for each antibody:
    i) 100 nM
    ii) 50 nM
    iii) 25 nM
    iv) 12.5 nM
    v) 6.25 nM
    vi) 3.125 nM.
2.4 Control Assay:
    Test antibodies for non-specific binding to streptavadin (FcI) before continuing with kinetic study. Use highest concentration of antibody to be used in kinetic assay (1OO nM in HBS-EP)

2.5 Immobilisation of Biotinylated-Peptide 23 (C5aR peptide) to SA Sensor Chip Fc2:
    Prepare Biot-peptide in HBS-EP at 1 µg/mL. Immobilise to Fc2 with manual injections about 1000 RU.
2.6 Antibody Kinetics Assay:
    Using the Kinetic Analysis Wizard, follow the prompts and enter the assay parameters as outlined below:
2.6.1 Enter concentration series to run:
    i.e. 3.125, 6.25, 12.5, 25, 50, 100 nM. Run samples in duplicate.
2.6.2 Select "Direct Binding Assay"
2.6.3 Select: "Concentration Series"
2.6.4 Enter the following parameters in dialogue box:
    Use Fc2, with FcI as reference
    Flow rate: 30 µl/min
    Injection time: 2 min
    Stabilisation time: 10 min
    Dissociation time: 20 min
    Select: "run samples as entered".
    Select: "next".
2.6.5 Regeneration method:
    Single injection
    Flow rate: 30 µl/min
    Regeneration buffer: 100 mM HCl
    Injection time: 2 min
    Stabilisation time after regeneration: 2 min.
2.6.6 Place antibodies and regeneration buffer in designated rack positions.
2.6.7 Run Wizard.

Calciumflux Assay

Freshly isolated human neutrophils were loaded with Fluo-3AM (Molecular Probes) for 30 min at 37° C. as previously described (Ponath, et al. *J. Clin. Invest.* 91:604-612 (1996)). Samples were run on a FACSCalibur™ flow cytometer and linear fluorescence intensities were measured over time.

Chemotaxis Assays

Human or mouse neutrophils ($1-2 \times 10^5$ cells per well) suspended in chemotaxis buffer (RPMI 1640 with 50% M1 99 (SIGMA) and 2% Fetal calf serum (HyClone) were placed in the upper chamber of a 12-well transwell plates (Corning Costar Co.) and allowed to migrate for 30 min across a 3 µm filter into the lower chamber containing human or mouse C5a. The number of migrated cells was enumerated on FACSCalibur™ by counting for 60 seconds. Tight forward angle and side scatter gates were set to exclude debris or irrelevant cells.

Construction of Cell Lines Expressing Chimeric Human/Mouse CSaRs

Chimeric human/mouse C5a receptors were constructed using a modified PCR-based overlap extension technique (Wurch, et al. *Mol. Pharmacol.* 54:1088-1096 (1998)). Briefly, different fragments of the human or mouse C5aR gene were amplified by PCR. Overlapping fragments were combined, denatured and re-annealed and amplified by second round of PCR. Full-length chimeric receptor sequences with appropriate restriction enzyme sites were amplified in a third PCR step and cloned into pcDNA3.1(+) (Invitrogen) for expression. PCR primers were designed according to the human C5aR and mouse C5aR gene sequences (Genebank accession numbers M62505 and S46665 respectively). The primers comprised adjacent human and mouse C5aR sequences (Table 1).

TABLE 1

The sequences of the PCR primers used to construct the chimeric mouse/human C5a receptors are shown. The sequence in red is from the human C5aR gene and the blue sequence corresponds to mouse C5aR respectively. The C5aR gene 5' end forward primer incorporates a Kozak sequence (underlined) upstream of the ATG and a HindIII site (bold). The 3' reverse primer incorporates a XbaI site (bold) to facilitate cloning into the expression vector.

| Primer | Primer sequences (5' > 3') |
|---|---|
| HuC5aREX1.f | CGTTTAAACTTAAGCTTGCCACCATGGACCCCATAGATAACAGCAG (SEQ ID NO: 10) |
| HuC5aRIC1.f | GGCAACCTGGGGATGTTGCAGCCTTGGTCATCTTTGCAGTC (SEQ ID NO: 11) |
| HuC5aRIC1.r | CCAGTAGTTATGATTTAAAACGGTCGTGAACAAGATGGGCAGCG (SEQ ID NO: 12) |
| HuC5aRIC2.f | ATGCCACCGCCTGTATAGTCCTGCCCTCCCTCATCCTGCTC (SEQ ID NO: 13) |
| HuC5aRIC2.r | CCTTATATGCCTCCCGGTACACGAAGGAGGGTATGGTCAGCAG (SEQ ID NO: 14) |
| HuC5aRIC3.f | AGAAGGCTGTGGCCATCCTGCGGCTGGTCCTGGGCTTCC (SEQ ID NO: 15) |
| HuC5aRIC3.r | GGCAGCCACGCTATCATCACCCCCGTCACCTGGTAGGGC (SEQ ID NO: 16) |
| HuC5aRIC4.f | AAGAGGGTGGAGAAGCTGAACTCCCTGTGTGTCTCCTTTGCC (SEQ ID NO: 17) |
| HuC5aRIC4.r | CCTCTAGAGTTAGGCCGGGGCCAC (SEQ ID NO: 18) |
| MuC5aREX1.r | GACTGCAAAGATGACCAAGGCTGCAACATCCCCAGGTTGCC (SEQ ID NO: 19) |
| MuC5aREX2.f | CGCTGCCCATCTTGTTCACGACCGTTTTAAATCATAACTACTGG (SEQ ID NO: 20) |
| MuC5aREX2.r | AGCAGGATGAGGGAGGGCAGGACTATACAGGCGGTGGCATC (SEQ ID NO: 21) |
| MuC5aREX3.f | CTGCTGACCATACCCTCCTTCGTGTACCGGGAGGCATATAAG (SEQ ID NO: 22) |
| MuC5aREX3.r | AGGAAGCCCAGGACCAGCCGCAGGATGGCCACAGCCTTC (SEQ ID NO: 23) |
| MuC5aREX4.f | GCCCTACCAGGTGACGGGGGTGATGATAGCGTGGCTGCC (SEQ ID NO: 24) |
| MuC5aREX4.r | GGCAAAGGAGACACACAGGGAGTTCAGCTTCTCCACCCTCTTC (SEQ ID NO: 25) |

Epitope Analysis with Synthetic Peptides

Two sets of peptides with N-terminal biotin and spacer GSGS were synthesized in immobilized form on plastic pins (Mimotopes Pty Ltd, Melbourne, Australia). The first set contained all possible 12 mers from the human C5aR second extracellular loop, each offset by one amino acid. The second set were 12 mers of the sequence VREEYFPPKVLC (SEQ ID NO: 32) each with one residue substituted by alanine. Peptides were initially reconstituted in 200 µl 60% DMSO and subsequently diluted in PBS to give a final concentration of 10 µg/ml for direct ELISA.

Peptide ELISA

Streptavidin-coated microtiter plates (NUNC) were coated with 10 µg/ml of peptide/well in a volume of 200 µl, and incubated at 4° C. overnight. Plates were washed three times with ELISA wash buffer (0.05% Tween 20 in PBS). MAbs were added at 2.5 µg/ml, and plates were incubated for 3 hrs at room temperature. HRP-conjugated rabbit anti-mouse IgG antibody diluted 1:1000 in ELISA wash buffer was used for detection. Plates were developed using TMB (3,3',5,5' tetramethyl benzidine, SIGMA) and read at A 40 nm.

Transfection of Expression Vectors into L1.2 Cells

Mouse L1.2 cells were grown in RPMI 1640 (GIBCO) supplemented with 10% Fetal calf serum (HyClone), and transfected using Lipofectamine™ 2000 (Invitrogen) according to the manufacturer's directions.

KZBxN Rheumatoid Arthritis Model

Serum was collected from K/BxN arthritic mice as previously described (Korganow et al. *Immun.* 10:451-461 (1999)). Experimental arthritis was induced in recipient mice by injecting 150 µl serum i.p. on days 0 and 2, and disease progress was monitored as described (Lee et al. *Science* 297: 1689-1692 (2002)) Ankle thickness and clinical scores were determined daily. The clinical score was calculated for each mouse by summing the scores for the four paws: 0—normal, 1—slight redness, 2—red and some swelling, 3—red and major swelling. Anti-hC5aR or isotype control mAbs (1-10 mg/kg in PBS) were injected i.p. on day −1 and 1 (preventative treatment) or day 5 (therapeutic treatment).

Statistical Analysis

The statistical significance of differences between independent control and treatment groups in the KxB/N model were determined using the Kruskal-Wallis test, followed bypost hoc analysis with Dunn's Multiple Comparison Test.

Example 1

Generation of mAbs to C5aR Using Transfected L1.2 Cells (Comparative Example)

Figure 1:
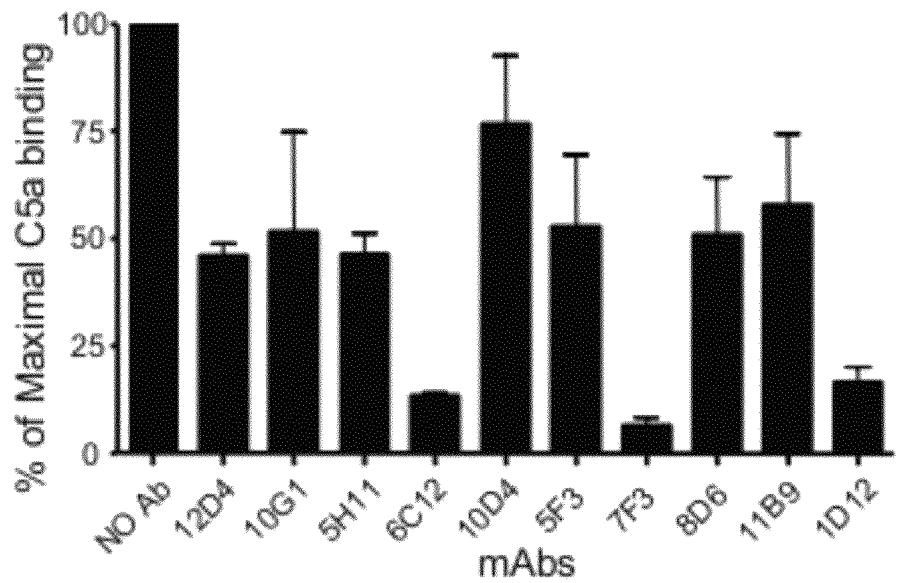
FIG. 1. The anti-human C5aR mAbs generated from mice immunized with L1.2/hC5aR cells inhibited binding of $^{125}$I-C5a to human neutrophils to varying degrees. Error bar indicates SD.

We raised mAbs to hC5aR, firstly by using a known approach for chemoattractant receptors (Heath, et al. *J. Clin. Invest.* 99:178-184 (1997); Qin, et al. *J. Clin. Invest.* 101:746-754 (1998); Wu, et al. (1997); Qin, et al. *Eur. J. Immunol.* 26:640-647 (1996)). Mice were immunized with L1.2 cells (a mouse B cell lymphoma line) expressing very high levels of hC5aR (about 80,000 receptors per cell). Five fusions were performed and more than 40 different mAbs identified that reacted specifically with hC5aR transfectants but not with transfectants expressing other closely related chemoattractant receptors, such as CXCR1, CXCR2, or the other C5a binding receptor, C5L2 (Gerard et al. *J. Biol. Chem.* 280(48): 39677-39680 (2005)). A number of these mAbs inhibited $^{125}$I-labeled human C5a binding to hC5aR transfectants. The lead mAb identified, 7F3, showed potent inhibition of C5a binding (FIG. 1), inhibited chemotaxis of human neutrophils to C5a in a chemotaxis assay and blocked C5a-induced calcium flux in human neutrophils (data not shown).

Example 2

Generation of mAbs to C5aR Using Neutrophils from hC5aR Knock-in Mice

Figure 2:
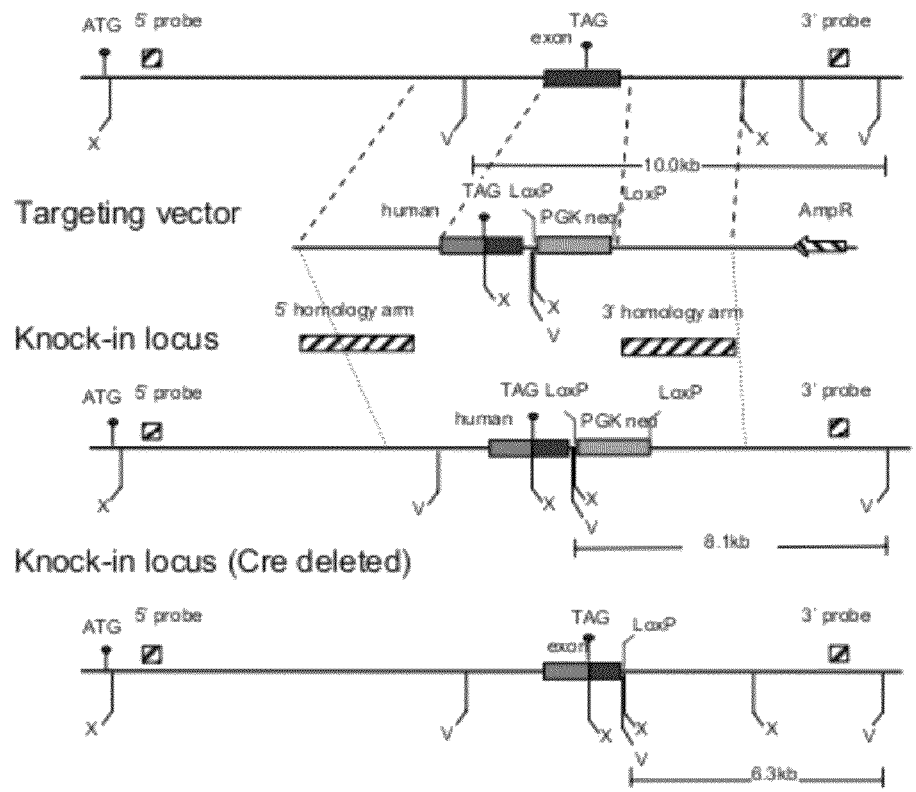
FIG. 2. Map of C5aR locus in wild-type mouse and targeting vector used to construct hC5aR knock-in mice. The mouse C5aR gene exon 3 CDS was precisely replaced with the human C5aR gene exon 3 CDS in the targeting vector. Mouse C5aR gene flanking sequences allowing homologous recombination. The selection marker PGKneo flanked by loxP sites was deleted from the first knock-in mouse using Cre. The 3' and 5' probes were used to confirm the targeting vector had recombined into the mouse C5aR locus correctly. X, Xbal; V, EcoRV.
Figure 3:
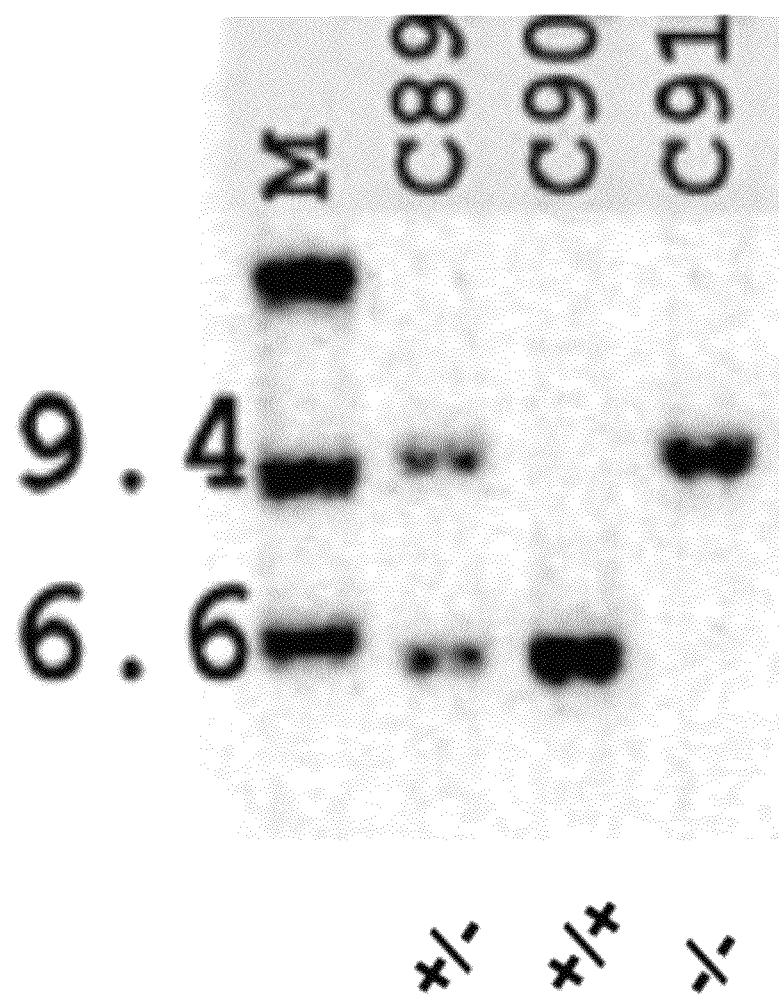
FIG. 3. Southern blot of EcoRV digested genomic DNA from the tails of mice from a cross between heterozygous hC5aR knock-in mice (hC5R1$^+$). The blot was hybridized with 3' probe, which distinguishes between the mouse C5aR allele (10.0 kb) and the hC5aRknock-in allele (8.1 kb).
Figure 4:
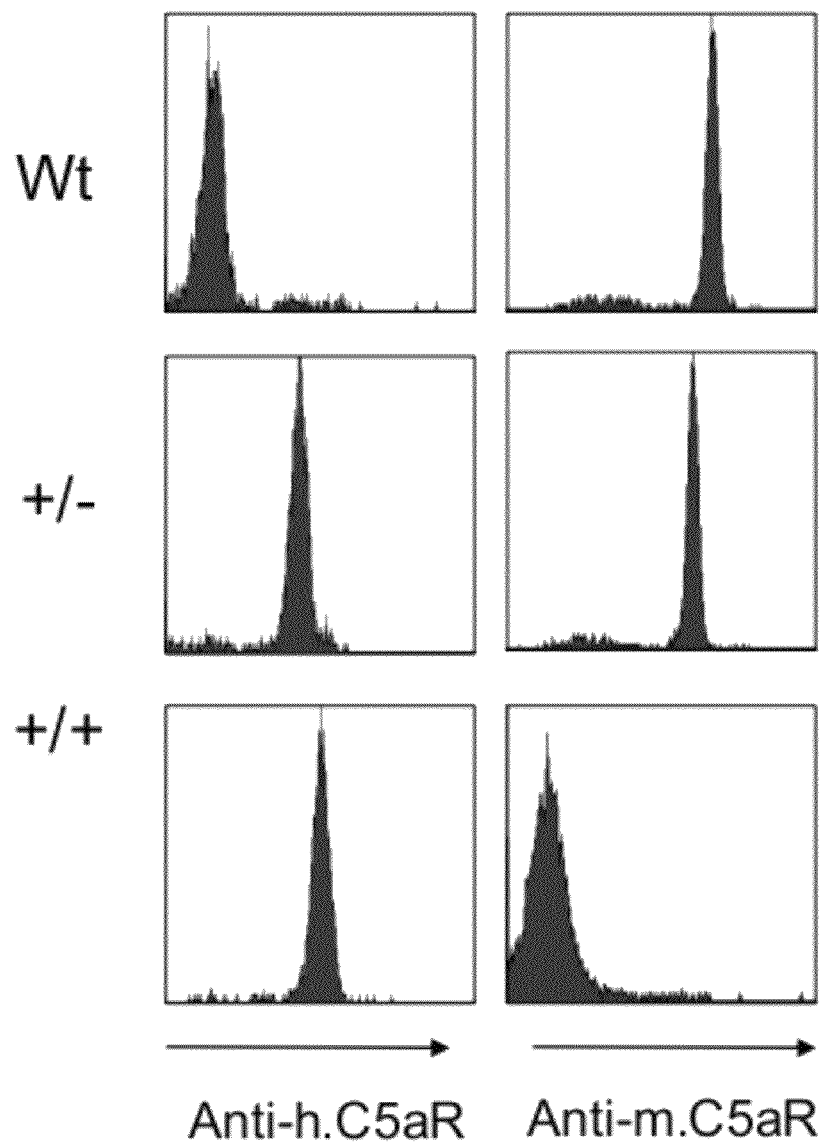
FIG. 4. Expression of C5aR on hC5R1$^{+/+}$, hC5R1$^{\pm}$ and wild-type mouse neutrophils. Neutrophils were stained with FITC-conjugated anti-human C5aR mAb (7F3) or anti-mouse C5aR mAb 20/70.

In a second approach to develop potent anti-C5aR mAbs, human C5aR knock-in mice were generated by targeted-homologous recombination at the mouse C5aR gene (C5R1). Simultaneous deletion of the endogenous C5aR coding sequence and its replacement with hC5aR coding sequence was achieved by transfecting mouse embryonic stem cells (ES) cells with targeting construct (FIG. 2). Two ES clones out of 672 screened were identified as containing the correctly targeted hC5aR sequence. Germline transmission of the hC5aR transgene was achieved, and 5 chimeric mice were produced from these ES cells thus establishing the hC5aR knock-in line. The PGK-neo gene flanked by loxP sites was deleted from the knock-in locus using a BL/6 Cre deleter strain. Mice homozygous for the human C5aR transgene (hCSR1$^{++}$) were identified by Southern blot (FIG. 3). Neutrophils from these mice were shown to express very high levels of hC5aR, as judged by FACS staining with anti-hC5aR mAbs (FIG. 4). Neutrophils from wild-type mice were unstained by anti-human C5aR mAb 7F3, but were stained intensely by an anti-mouse C5aR mAb, 20/70 (Soruri et al. *J. Immunol.* 170:3306-3314 (2003)) (FIG. 4). Human and mouse C5aRs share only 65% homology, but importantly for the development of hC5aR knock-in mice, mouse and human C5a binds to human C5aR with similar affinity (Gerard, et al. (1992)) (and our unpublished observations). Neutrophils from hC5R1$^{+/+}$ mice migrated to both human and mouse C5a in a similar fashion.

From one fusion we generated numerous hC5aR-specific mAbs. The anti-C5aR mAbs generated by immunization of wild-type mice with neutrophils from hC5R1$^{+/+}$ mice were all distinct, in that the amino acid sequences of the heavy chain variable regions were all distinct, indicating they originated from separate clones.

Figure 5:
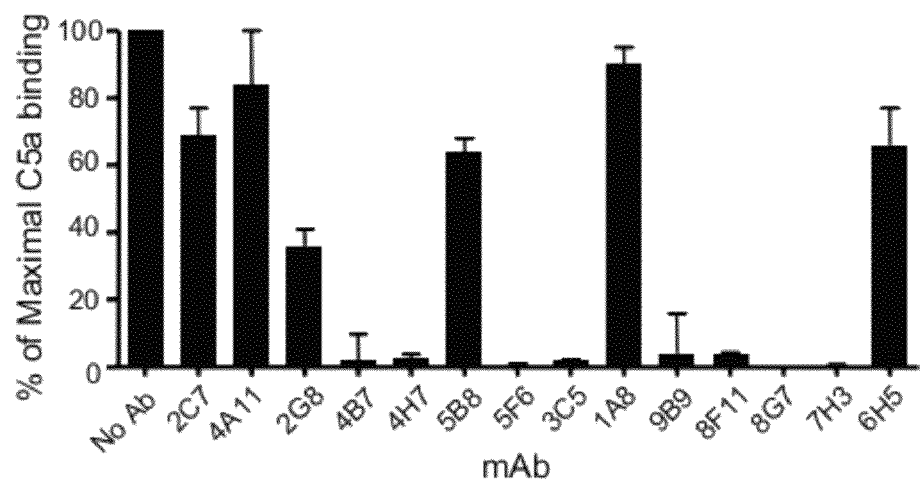
FIG. 5. Antibodies generated from neutrophils of hC5aR$^{+/+}$ mice showed a broad spectrum of $^{125}$I-C5a binding inhibition, ranging from complete inhibition to partial or little inhibition, depending on the mAb clone. Results are representative of at least two independent experiment for each antibody and error bar indicates s.e.m.
Figure 6:
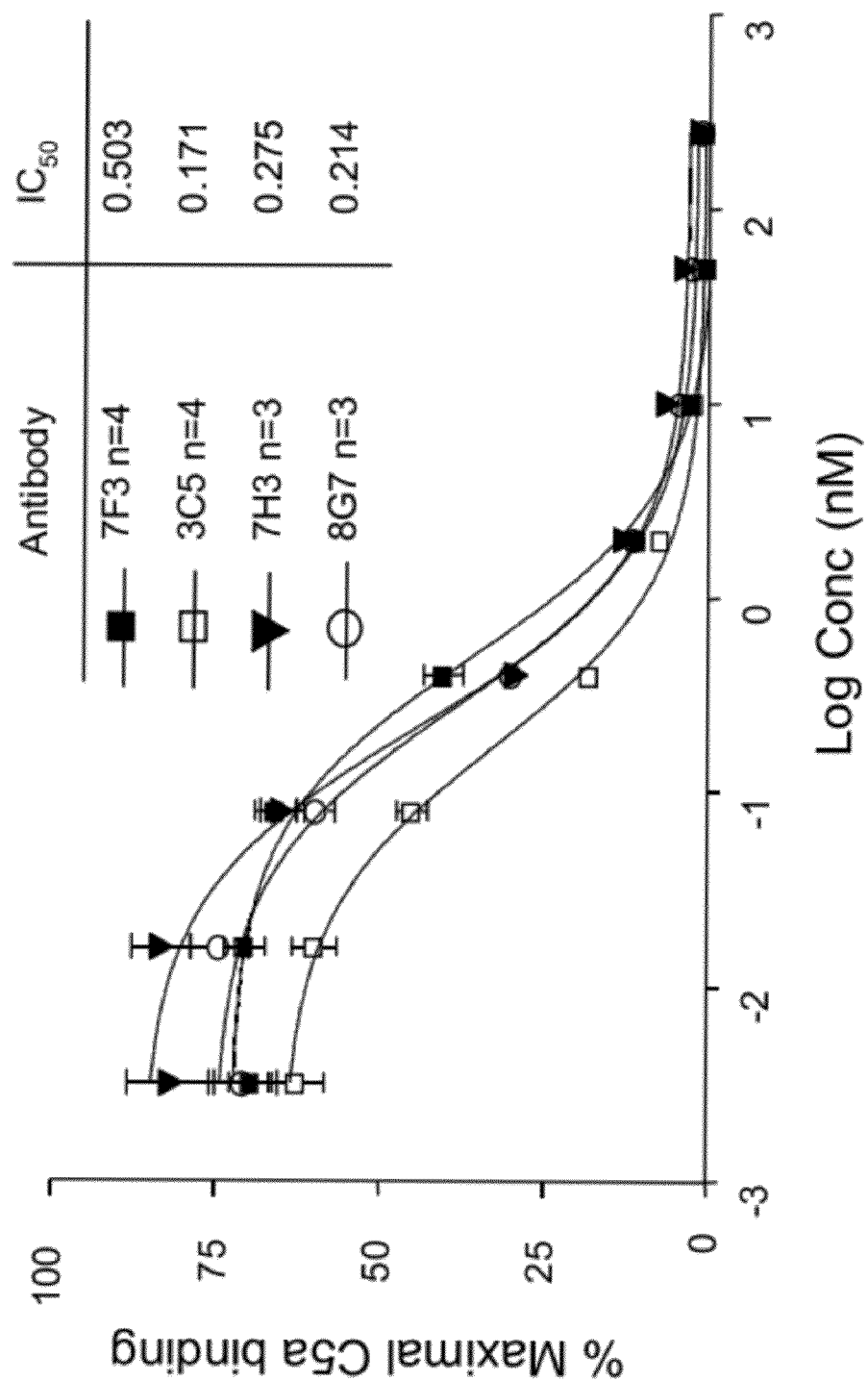
FIG. 6. Anti-C5aR mAbs have sub-nanomolar IC$_{50}$ values. Antibodies generated using hC5R1$^{+/+}$ mice neutrophils (3C5, 7H3 and 8G7) showed 5-10 fold lower IC$_{50}$ than the best mAb generated using L1.2/hC5aR transfectants (7F3). IC$_{50}$ values were determined from 3 or 4 independent competitive $^{125}$I-C5a ligand binding experiments.
Figure 7:
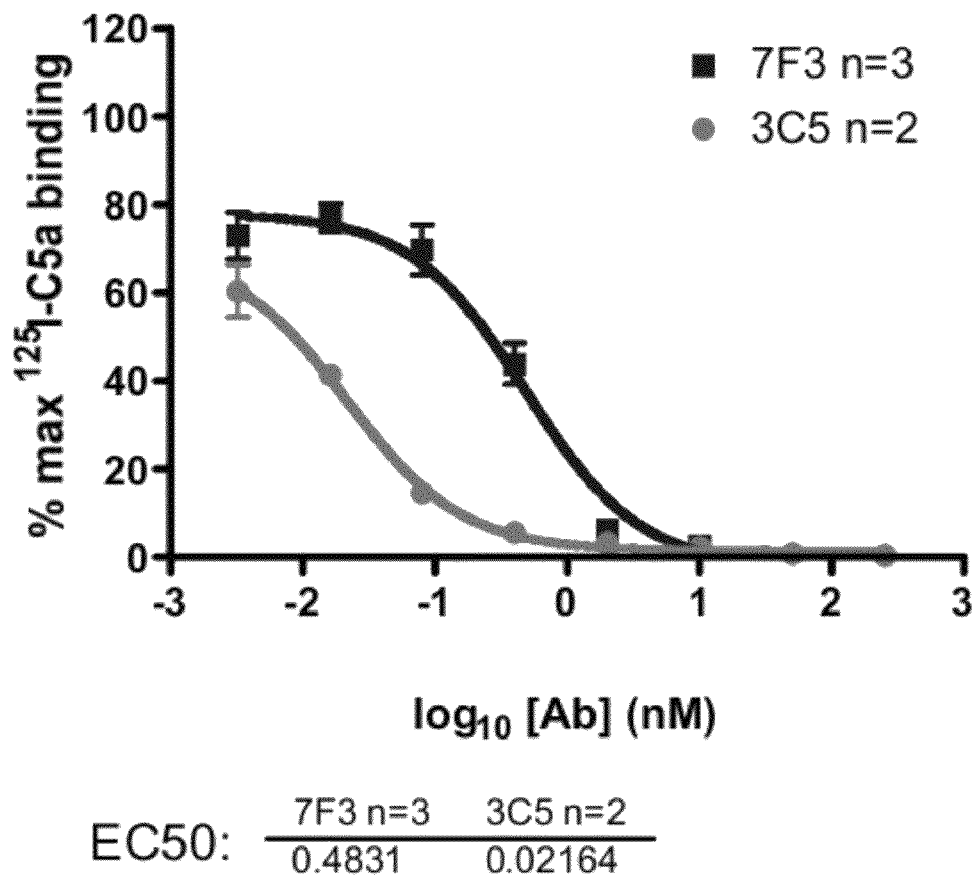
FIG. 7. Competitive ligand binding assay showing $^{125}$I-C5a displacement from hC5aR on hC5aR-transfected L1.2 cells with 7F3 or 3C5. EC$_{50}$ values were determined from 2 or 3 independent experiments.

Ligand binding assays revealed that many of these mAbs showed superior inhibition of $^{125}$I-labelled C5a binding to human neutrophils than mAb 7F3. Antibodies generated from neutrophils of hC5aR$^{+/+}$ mice showed a broad spectrum of inhibition of $^{125}$I-C5a binding to neutrophils, ranging from substantially complete inhibition (e.g. 3.5, 8G7, 7H3) to partial or little inhibition, depending on the mAb clone (FIG. 5). The most potent inhibitor, mAb 3C5, had an IC$_{50}$ of 171 pM, in comparison to an IC$_{50}$ for mAb 7F3 of 503 pM (FIG. 6). Further competitive ligand binding studies were conducted to measure $^{125}$I-C5a displacement from hC5aR on hC5aR-transfected L1.2 cells with 7F3 or 3C5. Again, 3C5 (EC50: 0.021 nM) showed a substantially higher affinity for C5aR than 7F3 (EC$_{50}$: 0.48 nM) (FIG. 7).

Example 3

Characterisation of C5aR Epitope Bound by mAbs

Figure 9:
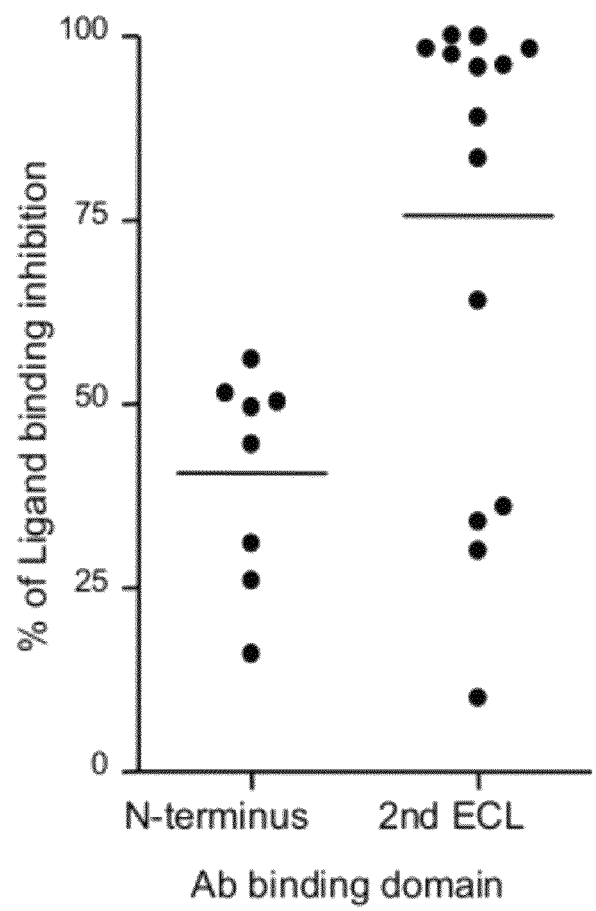
FIG. 9. Dot plot showing the degree to which each individual anti-hC5aR mAb inhibited C5a binding to human neutrophils. MAbs are grouped according to the receptor domain they recognised. The most potent blocking mAbs (those that inhibit C5a binding by >90%) all mapped to 2nd extracellular loop of hC5aR.
Figure 10:
FIG. 10. Mapping of antibody binding sites on hC5aR 2nd extracellular loop by peptide ELISA. MAb 7F3 and 3C5 bound to all of the overlapping peptides from hC5aR 2nd extracellular loop containing the sequence $^{179}$EEYFPP$^{184}$ (SEQ ID NO: 27).

The use of hC5aR transfectants and mouse neutrophils expressing hC5aR allowed the generation of mAbs recognizing, potentially, any of the extracellular domains, as well as epitopes reliant on tertiary structure. We therefore determined the critical epitopes on hC5aR, recognized by the blocking mAbs we have generated. Since these antibodies recognize human but not mouse C5aR, we constructed a panel of human/mouse C5aR chimeric receptors (FIG. 8). Single or multiple extracellular domains of human C5aR were sequentially replaced by the homologous region from mouse C5aR using an overlapping extension PCR method (Shevchuk, et al. *Nucleic Acids Res.* 32:9 (2004)). Chimeric receptors were expressed in mouse L1.2 cells and mAb reactivity was determined by FACS staining All antibodies with the most potent blocking activity, including mAbs 7F3, 3G5, 7H3 and 8G7, bound to the second extracellular loop of hC5aR (FIG. 9). To define the precise contact residues of the most potent blocking antibodies on C5aR second extracellular loop, we performed peptide scan analyses using a set of 12-mer peptides, each overlapping by 11 amino acids, covering the second extracellular loop of hC5aR, and ELISA. mAbs 3C5 and 7F3 showed strong binding to seven peptides from no. 1 to no. 7, containing the common hexapeptide sequence 179EEYFPP184 (FIG. 10). The epitope 179EEYFPP184 (SEQ ID NO: 27) was further studied using alanine substitution of every amino acid spanning this peptide region. FIGS. 11A and 11B show that amino acids E$^{179}$, E$^{180}$, Y$^{181}$, and F$^{182}$ were critical for peptide recognition by mAbs 7F3, 3C5, 8G7 and 7H3. Thus, of the many mAbs generated by us against hC5aR, the most potent inhibitors of C5a binding or function all mapped to a very specific region in the second extracellular loop of C5aR.

Example 4

MAb Binding Affinities

BIACore™ analysis was used to determine binding affinities of antibodies 7F3, 3C5, 8G7 and 7H3 to peptide 23 (2nd extracellular loop, residues 173 to 205 of human C5aR-LYRVVREEYFPPKVLCGVDYSHDKRRERAVAIV (SEQ ID No: 2)). Results are shown in FIG. 12 and summarized in Table 2.

TABLE 2

Summary of BIACore data for range of anti-C5aR mAbs

| | Association (on) Rate ka (1/Ms) | Dissociation (off) Rate kd (1/s) | Binding Affinity KA (1/M) | Binding Affinity KD (nM) |
|---|---|---|---|---|
| 7H3-N9 | 5.95E+05 | 9.95E-03 | 5.97E+07 | 16.7 |
| 3C5 | 3.30E+06 | 1.60E-03 | 2.10E+09 | 0.48 |
| 8G7-M6 | 3.70E+06 | 5.90E-03 | 6.30E+08 | 1.6 |
| 7F3 | 6.40E+05 | 4.50E-04 | 1.40E+09 | 0.7 |
| 2D7 (mIgG2a ctrl) | 4.60E+03 | 1.90E-04 | 2.50E+07 | 40 |
| 6G7 (mIgG3 ctrl) | 1.90E+04 | 2.60E-04 | 7.20E+07 | 14 |

Additional BIACore analyses were performed to compare binding affinities of antibodies 7F3 and 3C5 to peptide 23 under varying conditions. Results of these additional analyses are shown in Table 3. The conditions for these additional BIAcore experiments were as described above under "Experimental Details" with the following modifications:

Experiment 2: Antibody concentrations included in kinetic analysis—100 nM-0.78 nM; 20 min dissociation.
Experiment 3: Antibody concentrations included in kinetic analysis—7F3: 25 nM-0.78 nM; 3C5: 6.25nM-0.78nM; 5 min dissociation.
Experiment 4: Antibody concentrations included in kinetic analysis—7F3: 25 nM-1.56 nM; 3C5: 6.25 nM-0.4 nM; 1 min association, 3 min dissociation.

TABLE 3

Summary of Additional BIACore data for 7F3 and 3C5

| Experiment | mAb | Association (on) Rate ka (1/Ms) | Dissociation (off) Rate kd (1/s) | Binding Affinity KA (1/M) | Binding Affinity KD (nM) |
|---|---|---|---|---|---|
| 1. | 7F3 | 2.10E+05 | 3.80E-04 | 5.40E+08 | 1.80 |
|  | 3C5 | 6.80E+05 | 5.20E-04 | 1.30E+09 | 0.76 |
| 2. | 7F3 | 2.90E+05 | 3.50E-04 | 8.10E+08 | 1.20 |
|  | 3C5 | 1.50E+06 | 7.00E-04 | 2.20E+09 | 0.45 |
| 3. | 7F3 | 3.32E+05 | 4.62E-04 | 7.19E+08 | 1.39 |
|  | 3C5 | 1.06E+06 | 1.11E-03 | 9.60E+08 | 1.04 |
| 4. | 7F3 | 2.86E+05 | 5.98E-04 | 4.79E+08 | 2.09 |
|  | 3C5 | 1.03E+06 | 1.44E-03 | 7.16E+08 | 1.40 |

These results show that 3C5 has an approximately 1.5 fold improved affinity for the C5aR peptide over 7F3.

Example 5

Testing of Anti-hC5aR mAbs in a Mouse Rheumatoid Arthritis Model

The development of transgenic mice expressing human molecules is a convenient means to test new human therapeutics, designed for use in humans, in appropriate animal models. C5aR plays an essential role in pathogenesis of inflammatory arthritis in mice. For instance C5aR-deficient mice are protected from arthritis induced by either anti-glucose 6-phosphate isomerase auto-antibodies (Ji, et al. *Immun.* 16:157-168 (2002)) or type II collagen mAbs (Grant, et al. *J. Exp. Med.* 196:1461-1471 (2002)). Anti-hC5aR mAbs were tested for their ability to protect or reverse the progression of experimental arthritis in hC5R1$^{+/+}$ mice. Transfer of serum from arthritic K/BxN mice to healthy mice induces a joint-specific inflammatory reaction that mimics the K/BxN disease (Kouskoff, et al. *Cell* 87:8 11-822 (1996); Korganow, et al. *Immun.* 10:451-461 (1999)). The hC5R1$^{+/+}$ mice were pre-treated with either anti-hC5aR mAb or isotype matched control mAb on days −1 and 1 and K/BxN serum was injected intraperitoneally (i.p.) on day 0 and 2. After serum transfer, mice treated with control antibody exhibited typical clinical arthritis with joint swelling and inflammatory infiltrates, whereas mice treated with an anti-hC5aR mAb showed a complete absence of inflammation, clinically or histologically. There was no observable difference between hC5R1$^{+/+}$ mice and control littermates in the development of disease (data not shown), indicating that the human C5aR was fully functional, as disease in the KxB/N model is dependent on C5aR (Ji, et al. *Immun.* 16:157-168 (2002); Grant, et al. *J. Exp. Med.* 196:1461-1471 (2002)). More importantly, when antibody was administered 5 days after disease induction, we observed a significant reversal of established inflammation. The effects of mAbs raised against hC5aR-expressing mouse neutrophils (3C5 and 8G7) lasted longer than mAb 7F3 (FIGS. 13 and 14). As little as 1 mg/kg of mAb 3C5 was capable of reversing inflammation and providing sustained inhibition.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An antibody comprising:
   (i) a variable heavy chain sequence as shown in SEQ ID NO:3;
   (ii) a variable light chain sequence as shown in SEQ ID NO:4; or
   (iii) a variable heavy chain region comprising the CDR1, CDR2, and CDR3 loop sequences of a variable heavy chain sequence as shown in SEQ ID NO:3 and a variable light chain region comprising the CDR1, CDR2, and CDR3 loop sequences of a variable light chain sequence as shown in SEQ ID NO:4;
   wherein the antibody reduces or inhibits the binding of C5a to C5aR.

2. An antibody according to claim 1, that binds to human C5aR, or a fragment thereof comprising the sequence set forth in SEQ ID NO: 27, with:
   (i) an IC$_{50}$ value that is at least 1.5 fold lower than that of MAb7F3 (produced by a hybridoma deposited with ECACC under accession number 00110609) when determined under identical conditions; or
   (ii) an association constant (Kon) that is at least 1.5 fold higher than that of MAb7F3 when determined under identical conditions; or
   (iii) a K$_d$ affinity constant that is at least 1.3 fold lower than that of MAb7F3 when determined under identical conditions.

3. An antibody according to claim 1 that binds to human C5aR, or a fragment thereof, comprising the sequence set forth in SEQ ID NO: 27 with:
   (i) an IC$_{50}$ value that is less than 500 pM; or
   (ii) an association constant (Kon) that is at least 6.8×10$^5$ M$^{-1}$s$^{-1}$; or
   (iii) a K$_d$ affinity constant that is less than 1.4 nM.

4. An antibody according to claim 2, wherein the fragment of C5aR is a peptide comprising the sequence LYRVVREEYFPPKVLCGVDYSHDKRRERAVAIV (SEQ ID NO: 2).

5. An antibody comprising:
   (i) a variable heavy chain sequence as shown in SEQ ID NO:5;
   (ii) a variable light chain sequence as shown in SEQ ID NO:6; or
   (iii) a variable heavy chain region comprising the CDR1, CDR2, and CDR3 loop sequences of a variable heavy chain sequence as shown in SEQ ID NO:5 and a variable light chain region comprising the CDR1, CDR2, and CDR3 loop sequences of a variable light chain sequence as shown in SEQ ID NO:6;
   wherein the antibody reduces or inhibits the binding of C5a to C5aR.

6. An antibody comprising:
   (i) a variable heavy chain sequence as shown in SEQ ID NO:7;
   (ii) a variable light chain sequence as shown in SEQ ID NO:8; or
   (iii) a variable heavy chain region comprising the CDR1, CDR2, and CDR3 loop sequences of a variable heavy chain sequence as shown in SEQ ID NO:7 and a variable light chain region comprising the CDR1, CDR2, and CDR3 loop sequences of a variable light chain sequence as shown in SEQ ID NO:8;

wherein the antibody reduces or inhibits the binding of C5a to C5aR.

7. A monoclonal antibody selected from the group consisting of:
   (i) an antibody comprising a variable heavy chain sequence as shown in SEQ ID NO: 3 and a variable light chain sequence as shown in SEQ ID NO: 4;
   (ii) an antibody produced by a hybridoma deposited with ECACC under accession number 06081801;
   (iii) an antibody comprising a variable heavy chain sequence as shown in SEQ ID NO: 5 and a variable light chain sequence as shown in SEQ ID NO: 6;
   (iv) an antibody produced by a hybridoma deposited with ECACC under accession number 06081802;
   (v) an antibody comprising a variable heavy chain sequence as shown in SEQ ID NO: 7 and a variable light chain sequence as shown in SEQ ID NO: 8; and
   (vi) an antibody produced by a hybridoma deposited with ECACC under accession number 06081803.

8. A hybridoma as deposited with ECACC under accession number 06081801, 06081802, or 06081803.

9. An isolated nucleic acid molecule comprising a sequence encoding an antibody of claim 1.

10. A composition comprising an antibody of claim 1 or claim 6 and a pharmaceutically acceptable carrier.

11. A method for detecting C5aR in a subject in a subject, the method comprising:
    contacting a sample obtained from the subject in vitro with a conjugate comprising the antibody of claim 1 and a detectable label; and
    detecting immunospecific binding between the conjugate and the sample by detecting the detectable label,
    wherein said detecting indicates the presence of C5aR in the subject.

12. A method of inhibiting the interaction of a cell bearing C5aR with C5a comprising contacting the cell with an antibody of claim 1.

13. A method of reducing or inhibiting interaction of C5aR with C5a in a subject having an autoimmune or inflammatory condition, comprising administering to the subject an antibody of claim 1.

14. A method of inhibiting leukocyte trafficking in a mammal in need thereof, comprising administering to the mammal an antibody of claim 1 in an amount effect to inhibit the migration of leukocyte trafficking in the mammal.

15. The antibody of claim 1, which is a monoclonal antibody, a recombinant antibody, a chimeric antibody or a humanized antibody.

16. The antibody of claim 5, which is a monoclonal antibody, a recombinant antibody, a chimeric antibody or a humanized antibody.

17. The antibody of claim 6, which is a monoclonal antibody, a recombinant antibody, a chimeric antibody or a humanized antibody.

18. A method of detecting and/or quantitating expression of C5aR by a cell, the method comprising:
    contacting a composition comprising a cell or fraction thereof with a conjugate comprising the antibody of claim 1 and a detecting label; and
    detecting immunospecific binding between the conjugate and the cell or fraction thereof by detecting the detecting label,
    wherein detecting the immunospecific binding detects and/or quantitates expression of C5aR by the cell.

* * * * *